United States Patent
Liang et al.

(10) Patent No.: US 11,633,721 B2
(45) Date of Patent: Apr. 25, 2023

(54) MULTILAYER MIXED OXIDE SUPPORTED CATALYST FOR OXIDATIVE COUPLING OF METHANE

(71) Applicant: SABIC Global Technologies B.V., Bergen op Zoom (NL)

(72) Inventors: Wugeng Liang, Sugar Land, TX (US); Luanyi Li, Sugar Land, TX (US); Hector Perez, Sugar Land, TX (US); Pankaj Gautam, Sugar Land, TX (US); David West, Sugar Land, TX (US)

(73) Assignee: Sabic Global Technologies, B.V., Bergen op Zoom (NL)

( * ) Notice: Subject to any disclaimer, the term of this patent is extended or adjusted under 35 U.S.C. 154(b) by 0 days.

(21) Appl. No.: 17/769,879

(22) PCT Filed: Sep. 21, 2020

(86) PCT No.: PCT/US2020/051725
§ 371 (c)(1),
(2) Date: Apr. 18, 2022

(87) PCT Pub. No.: WO2021/080717
PCT Pub. Date: Apr. 29, 2021

(65) Prior Publication Data
US 2022/0387973 A1    Dec. 8, 2022

Related U.S. Application Data

(60) Provisional application No. 62/924,508, filed on Oct. 22, 2019.

(51) Int. Cl.
*B01J 23/10* (2006.01)
*B01J 23/02* (2006.01)
(Continued)

(52) U.S. Cl.
CPC ............. *B01J 23/10* (2013.01); *B01J 23/02* (2013.01); *B01J 35/0006* (2013.01); *B01J 35/1009* (2013.01); *B01J 35/1014* (2013.01); *B01J 35/1038* (2013.01); *B01J 35/1042* (2013.01); *B01J 35/1061* (2013.01); *B01J 35/1066* (2013.01); *B01J 35/1071* (2013.01); *B01J 35/1076* (2013.01); *B01J 37/0205* (2013.01); *B01J 37/0228* (2013.01); *B01J 37/0236* (2013.01); *B01J 37/0244* (2013.01); *B01J 37/088* (2013.01); *C07C 2/84* (2013.01); *C07C 11/04* (2013.01); *B01J 2523/10* (2013.01);
(Continued)

(58) Field of Classification Search
CPC ... B01J 23/10; B01J 23/02; B01J 21/04; B01J 2523/00; B01J 2523/24; B01J 2523/31; B01J 2523/3706; B01J 2523/3725; B01J 2523/3787; B01J 37/0228; B01J 37/0236; B01J 37/0244; B01J 37/088; B01J 37/0205; B01J 35/0006; B01J 35/1009; B01J 35/1014; B01J 35/1038; B01J 35/1042; B01J 35/1061; B01J 35/1066; B01J 35/1071; B01J 35/1076; B01J 2523/04; B01J 2523/10; C07C 2/84; C07C 11/04; C07C 2521/12; C07C 2523/04; C07C 2523/06; C07C 2523/10; Y02P 20/52; Y02P 20/582
USPC ... 502/4, 302, 303, 304, 340, 341, 305, 306, 502/527.12, 527.13, 527.15; 585/502, 585/520, 521, 523, 530
See application file for complete search history.

(56) References Cited

U.S. PATENT DOCUMENTS 5,043,505 A    8/1991   Erekson et al.
5,712,217 A    1/1998   Choudhary et al.
(Continued)

FOREIGN PATENT DOCUMENTS

EP    0335130 A1   10/1989
EP    3194070 A2    7/2017
(Continued)

OTHER PUBLICATIONS

Office Action dated Dec. 8, 2021, U.S. Appl. No. 16/821,409, filed Mar. 17, 2020.
(Continued)

*Primary Examiner* — Elizabeth D Wood

(57) ABSTRACT

A multilayer supported oxidative coupling of methane (OCM) catalyst composition (support, first single oxide layer, one or more mixed oxide layers, optional second single oxide layer) characterized by formula $A_aZ_bE_cD_dO_x$/support; A is alkaline earth metal; Z is first rare earth element; E is second rare earth element; D is redox agent/third rare earth element; the first, second, third rare earth element are not the same; a=1.0; b=0.1-10.0; c=0.1-10.0; d=0-10.0; x balances oxidation states; first single oxide layer ($Z_{b1}O_{x1}$, b1=0.1-10.0; x1 balances oxidation states) contacts support and one or more mixed oxide layers; one or more mixed oxide layers ($A_{a2}Z_{b2}E_{c2}D_{d2}O_{x2}$, a2=1.0; b2=0.1-10.0; c2=0.1-10.0; d2=0-10.0; x2 balances oxidation states; $A_aZ_bE_cD_dO_x$ and $A_{a2}Z_{b2}E_{c2}D_{d2}O_{x2}$ are different) contacts first single oxide layer and optionally second single oxide layer, and second single oxide layer (AO), when present, contacts one or more mixed oxide layers and optionally first single oxide layer.

20 Claims, 2 Drawing Sheets

(51) Int. Cl.
  *B01J 37/02* (2006.01)
  *B01J 37/08* (2006.01)
  *C07C 2/84* (2006.01)
  *B01J 35/10* (2006.01)
  *B01J 35/00* (2006.01)
  *C07C 11/04* (2006.01)

(52) U.S. Cl.
  CPC ........ *B01J 2523/24* (2013.01); *B01J 2523/31* (2013.01); *B01J 2523/3706* (2013.01); *B01J 2523/3725* (2013.01); *B01J 2523/3787* (2013.01); *C07C 2521/12* (2013.01); *C07C 2523/04* (2013.01); *C07C 2523/06* (2013.01); *C07C 2523/10* (2013.01)

(56) References Cited

U.S. PATENT DOCUMENTS

| | | | |
|---|---|---|---|
| 6,087,545 | A | 7/2000 | Choudhary et al. |
| 9,963,402 | B2 | 5/2018 | Cizeron et al. |
| 11,439,984 | B2 | 9/2022 | Liang et al. |
| 2007/0083073 | A1 | 4/2007 | Bagherzadeh et al. |
| 2013/0023709 | A1 | 1/2013 | Cizeron et al. |
| 2016/0074844 | A1 | 3/2016 | Freer et al. |
| 2016/0107143 | A1 | 4/2016 | Schammel et al. |
| 2017/0014807 | A1 | 1/2017 | Liang et al. |
| 2017/0267605 | A1 | 9/2017 | Tanur et al. |
| 2018/0118637 | A1 | 5/2018 | Zurcher et al. |
| 2019/0077728 | A1 | 3/2019 | Cizeron et al. |
| 2019/0233364 | A1 | 8/2019 | Lange De Oliveira et al. |

FOREIGN PATENT DOCUMENTS

| | | |
|---|---|---|
| RU | 2144844 C1 | 1/2000 |
| RU | 2306177 C2 | 9/2007 |
| RU | 2435830 C1 | 12/2011 |
| RU | 2523013 C1 | 7/2014 |
| RU | 2783516 C1 | 11/2022 |
| WO | 03024595 A1 | 3/2003 |
| WO | 2013177461 A2 | 11/2013 |
| WO | 2016044428 A2 | 3/2016 |
| WO | 20180085820 A1 | 5/2018 |
| WO | 20180175535 A1 | 9/2018 |
| WO | 2018213183 A1 | 11/2018 |
| WO | 2019048404 A1 | 3/2019 |
| WO | 2021080716 A1 | 4/2021 |
| WO | 2021080717 A1 | 4/2021 |
| WO | 2021126414 A1 | 6/2021 |

OTHER PUBLICATIONS

Choudhary, Vasant R. et al., "Coupling of Exothermic and Endothermic Reactions in Oxidative Conversion of Natural Gas into Ethylene/Olefins over Diluted SrO/La2O3/SA5205 Catalyst", Industrial & Engineering Chemistry Research, 1997, pp. 3520-3527, vol. 36, No. 9, American Chemical Society.

Mulla, S.A.R et al., "Oxidative conversion of ethane to ethylene over supported SrO-promoted Er2O3 catalyst", Journal of Molecular Catalysis A: Chemical, 2004, pp. 259-262, vol. 223, Elsevier B.V.

Choudhary, Vasant R. et al., "Oxidative Coupling of Methane over a Sr-Promoted La2O3 Catalyst Supported on a Low Surface Area Porous Catalyst Carrier", Industrial & Engineering Chemistry Research, 1997, pp. 3594-3601, vol. 36, No. 9, American Chemical Society.

Choudhary, Vasant R. et al., "Oxidative Coupling of Methane over Supported La2O3 and La-Promoted MgO Catalysts: Influence of Catalyst—Support Interactions", Industrial & Engineering Chemistry Research, 1997, pp. 2096-2100, vol. 36, No. 6, American Chemical Society.

Choudhary, V.R. et al., "Oxidative Coupling of Methane over SrO Deposited on Different Commercial Supports Precoated with La2O3", Industrial & Engineering Chemistry Research, 1998, pp. 2142-2147, vol. 37, No. 6, American Chemical Society.

Mulla, S.A.R. et al., "Conversion of ethane to ethylene in presence of limited O2 over supported SrO promoted Sm2O3 catalyst", Indian Journal of Chemical Technology, Nov. 2003, pp. 615-618, vol. 10.

Asami, Kenji et al., "Selective Oxidative Coupling of Methane over Supported Lead Oxide Catalyst," Chemistry Letters, 1986, pp. 1233-1236, The Chemical Society of Japan.

Uphade, B.S. et al., "Influence of metal oxide—Support interactions in supported la-promoted CaO catalysts for oxidative coupling of methane," Studies in Surface Science and Catalysis, 1998, pp. 1015-1021, vol. 113, Elsevier B.V. (Abstract Only).

Bytyn, W. et al., "Supported PbO catalysts for the oxidative coupling of methane—The effect of surface acidity of the support on C2+ selectivity," Applied Catalysis, 1986, pp. 199-207, vol. 28, Elsevier B.V. (Abstract Only).

Fang, Xueping et al., "Oxidative Coupling of Methane on W—Mn Catalysts," Journal of Molecular Catalysis, 1992, pp. 255-261, vol. 8, No. 4.

Fang, Xueping et al., "Preparation and Characterization of Catalyst for Oxidative Coupling of Methane," Journal of Molecular Catalysis, 1992, pp. 427-433, vol. 6, No. 6.

Lee, Jong Yeol et al., "Scaled-up production of C2 hydrocarbons by the oxidative coupling of methane over pelletized Na2WO4/Mn/SiO2 catalysts: Observing hot spots for the selective process," Fuel, 2013, pp. 851-857, vol. 106, Elsevier Limited.

Arndt, Sebastian et al., "Mn—Na2WO4/SiO2 as Catalyst for the Oxidative Coupling of Methane. What is Really Known?," Applied Catalysis A: General, 2012, pp. 53-61, vols. 425-426, Elsevier.

Foreign Communication from Related Application—International Search Report and Written Opinion of the International Searching Authority, International Application No. PCT/US2020/051724, dated Jan. 22, 2021, 8 pages.

Foreign Communication from Related Application—International Search Report and Written Opinion of the International Searching Authority, International Application No. PCT/US2020/059840, dated Apr. 28, 2021, 13 pages.

Office Action issued on corresponding Russian Application dated Oct. 6, 2022, regarding Russian Application No. 2022113196, filed May 17, 2022, 24 pages.

Foreign Communication from Related Counterpart—Decision to Grant dated Oct. 27, 2022, Russian Application No. 2022113297, filed Sep. 21, 2020, 20 pages.

Filing Receipt, Specification and Drawings for U.S. Appl. No. 17/769,884, filed Apr. 18, 2022, entitled "Multilayer Mixed Oxide Supported Catalyst for Oxidative Coupling of Methane," 45 pages.

Filing Receipt, Specification and Drawings for U.S. Appl. No. 17/785,216, filed Jun. 14, 2022, entitled "OCM Catalyst Composition Having Improved Stability and Carbon Efficiency," 35 pages.

Foreign Communication from Related Application—International Search Report and Written Opinion of the International Searching Authority, International Application No. PCT/US2020/051725, dated Sep. 21, 2020, 8 pages.

MULTILAYER MIXED OXIDE SUPPORTED CATALYST FOR OXIDATIVE COUPLING OF METHANE

CROSS REFERENCE TO RELATED APPLICATIONS

This application is a filing under 35 U.S.C. 371 of International Application No. PCT/US2020/051725 filed Sep. 21, 2020, entitled "Multilayer Mixed Oxide Supported Catalyst for Oxidative Coupling of Methane" which claims priority to U.S. Provisional Application No. 62/924,508 filed Oct. 22, 2019, which applications are incorporated by reference herein in their entirety.

TECHNICAL FIELD

The present disclosure relates to catalyst compositions for oxidative coupling of methane (OCM), more specifically multilayer supported catalyst compositions based on mixed oxides for OCM, and methods of making and using same.

BACKGROUND

OCM has been the target of intense scientific and commercial interest for more than thirty years due to the tremendous potential of such technology to reduce costs, energy, and environmental emissions in the production of $C_2H_4$. There are conventional catalyst systems developed for OCM processes, but such catalyst systems have many shortcomings. For example, for commercial applications, high performance (e.g., high activity, high selectivity to desired products) of OCM catalysts is critical. Generally, for commercial applications of OCM catalysts, for example in commercial scale fixed bed reactors, OCM catalysts would have to be formed into pellets with required strength, shape and size, while retaining high performance. Conventional catalysts systems for OCM display performance problems when formed into pellets, such as a decrease in selectivity towards desired products (e.g., $C_{2+}$ hydrocarbons, $C_2H_4$) with scaling up to large reactors (e.g., industrial scale reactors), owing to pore structure changes (e.g., a decrease in pore volume) that lead to an increase in mass transfer resistance. Further, conventionally placing an OCM catalytically active material onto various supports that could provide for the required strength, shape and size, in order to form OCM catalysts for commercial applications has led to poor performance. Thus, there is an ongoing need for the development of catalyst compositions for OCM processes.

BRIEF DESCRIPTION OF THE DRAWINGS

For a detailed description of the preferred aspects of the disclosed methods, reference will now be made to the accompanying drawing in which.

DETAILED DESCRIPTION

Figure 1:
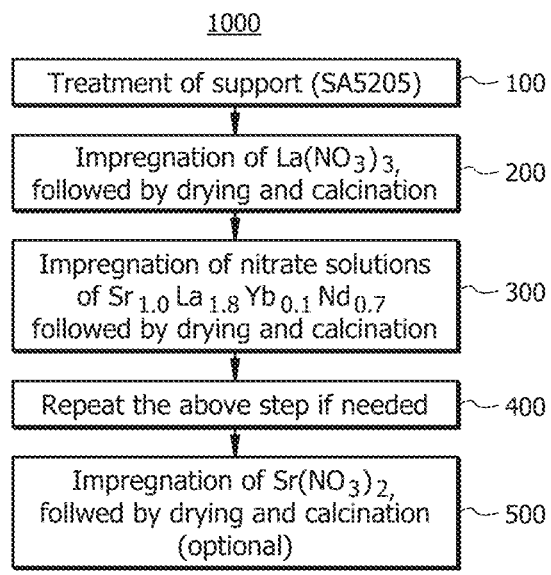
FIG. 1 illustrates a flow diagram of a method for making a multilayer supported oxidative coupling of the methane (OCM) catalyst composition.

Disclosed herein are multilayer supported oxidative coupling of methane (OCM) catalyst compositions and methods of making and using same. The multilayer supported OCM catalyst compositions comprise a structured multilayer supported multi-component rare earth metal oxides OCM catalyst with a significant improvement in the performance of the catalyst, when compared to conventional catalysts, wherein the multilayer supported OCM catalyst composition is suitable for large scale reactor applications.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "from more than 0 to an amount" means that the named component is present in some amount more than 0, and up to and including the higher named amount. The terms "a," "an," and "the" do not denote a limitation of quantity, but rather denote the presence of at least one of the referenced item. As used herein the singular forms "a," "an," and "the" include plural referents. Reference throughout the specification to "an aspect," "another aspect," "other aspects," "some aspects," and so forth, means that a particular element (e.g., feature, structure, property, and/or characteristic) described in connection with the aspect is included in at least an aspect described herein, and may or may not be present in other aspects. In addition, it is to be understood that the described element(s) can be combined in any suitable manner in the various aspects. As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like. As used herein, the terms "inhibiting" or "reducing" or "preventing" or "avoiding" or any variation of these terms, include any measurable decrease or complete inhibition to achieve a desired result. As used herein, the term "effective," means adequate to accomplish a desired, expected, or intended result. As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are inclusive or open-ended and do not exclude additional, unrecited elements or method steps.

Unless defined otherwise, technical and scientific terms used herein have the same meaning as is commonly understood by one of skill in the art. Compounds are described herein using standard nomenclature. For example, any position not substituted by any indicated group is understood to have its valency filled by a bond as indicated, or a hydrogen atom. A dash ("—") that is not between two letters or symbols is used to indicate a point of attachment for a substituent. For example, —CHO is attached through the carbon of the carbonyl group. As used herein, the terms "$C_X$ hydrocarbons" and "$C_x$s" are interchangeable and refer to any hydrocarbon having x number of carbon atoms (C). For example, the terms "$C_4$ hydrocarbons" and "$C_4$s" both refer to any hydrocarbons having exactly 4 carbon atoms, such as n-butane, iso-butane, cyclobutane, 1-butene, 2-butene, isobutylene, butadiene, and the like, or combinations thereof. As used herein, the term "$C_{x+}$ hydrocarbons" refers to any hydrocarbon having equal to or greater than x carbon atoms (C). For example, the term "$C_{2+}$ hydrocarbons" refers to any hydrocarbons having 2 or more carbon atoms, such as ethane, ethylene, $C_3$s, $C_4$s, $C_5$s, etc.

In an aspect, a multilayer supported OCM catalyst composition as disclosed herein can be characterized by the general formula $A_a Z_b E_c D_d O_x$/support, wherein the multilayer supported OCM catalyst composition comprises a support, a first single oxide layer, one or more mixed oxide layers, and an optional second single oxide layer; wherein A is an alkaline earth metal; wherein Z is a first rare earth element; wherein E is a second rare earth element; wherein D is a redox agent or a third rare earth element; wherein the first rare earth element, the second rare earth element, and the third rare earth element, when present, are not the same; wherein a is 1.0; wherein b is from about 0.1 to about 10.0, about 0.3 to about 10.0, about 0.5 to about 8, or about 1 to about 5; wherein c is from about 0.1 to about 10.0, about 0.1 to about 8, or about 0.5 to about 5; wherein d is from about 0 to about 10.0, about 0.1 to about 8, or about 0.5 to about 5; and wherein x balances the oxidation states. As will be appreciated by one of the skill in the art, and with the help of this disclosure, each of the A, Z, E and D can have multiple oxidation states within the multilayer supported OCM catalyst composition, and as such x can have any suitable value that allows for the oxygen anions to balance all the cations. Without wishing to be limited by theory, the different metals (A, Z, E, and D) present in the multilayer supported OCM catalyst composition as disclosed herein display synergetic effects in terms of conversion and selectivity. Further, and without wishing to be limited by theory, different ion radii and valences of the multiple metals (A, Z, E, and D) present in the multilayer supported OCM catalyst composition as disclosed herein can generate formation of uncompensated oxygen vacancies, which can lead to further improvement of catalyst performance, e.g., conversion, selectivity, stability, etc.

As will be appreciated by one of skill in the art, and with the help of this disclosure, and without wishing to be limited by theory, an OCM catalyst comprising a single metal might not provide all the necessary properties for an optimum OCM reaction (e.g., best OCM reaction outcome) at the best level, and as such conducting an optimum OCM reaction may require an OCM catalyst with tailored composition in terms of metals present, wherein the different metals can have optimum properties for various OCM reaction steps, and wherein the different metals can provide synergistically for achieving the best performance for the OCM catalyst in an OCM reaction.

Without wishing to be limited by theory, an OCM reaction can propagate by following a mechanism according to reactions (1)-(8):

$$[O]_s + CH_4 \rightarrow [OH]_s + CH_3 \cdot \quad (1)$$

$$2CH_3 \cdot \rightarrow C_2H_6 \quad (2)$$

$$CH_3 \cdot + O_2 \leftrightarrow CH_3O_2 \quad (3)$$

$$CH_3 \cdot + [O]_s \leftrightarrow [CH_3O]_s \quad (4)$$

$$2[OH]_s + 1/2 O_2 \rightarrow 2[O]_s + H_2O \quad (5)$$

$$C_2H_6 + 1/2 O_2 \rightarrow C_2H_4 + H_2O \quad (6)$$

$$C_2H_4 + 1/2 O_2 \rightarrow C_2H_2 + H_2O \quad (7)$$

$$C_2H_4 + 5/2 O_2 \rightarrow CO + CO_2 + 2H_2O \quad (8)$$

wherein "s" denotes a species adsorbed onto the catalyst surface. As will be appreciated by one of skill in the art, and with the help of this disclosure, two or more of reactions (1)-(8) can occur concurrently (as opposed to sequentially). According to reaction (1), the activation of methane occurs with the participation of active adsorbed oxygen sites $[O]_s$, leading to the formation of methyl radicals and adsorbed hydroxyl group $[OH]_s$. According to reaction (2), the coupling of methyl radicals to form the coupling product ethane ($C_2H_6$) occurs in gas phase; wherein reaction (2) has a low activation energy, and therefore, does not limit the overall reaction rate. According to reaction (3), methyl radicals can react with gas phase oxygen to form an oxygenate product $CH_3O_2$. According to reaction (4), methyl radicals can also re-adsorb onto the catalyst surface and react with surface oxygen (e.g., active adsorbed oxygen sites $[O]_s$) to form an oxygenate species $[CH_3O]_s$. The oxygenates formed according to reactions (3) and (4) can further form CO and $CO_2$, and as such the reaction steps according to reactions (3) and (4) are the main reactions controlling the selectivity of various OCM catalysts.

Further, and without wishing to be limited by theory, easy removal of methyl radicals from oxygen centers will result in increasing $C_{2+}$ selectivity; while oxygen centers that display strong bonding will promote the oxidation of methyl radicals via $[CH_3O]_s$, thereby leading to the formation of deep oxidation products ($CO_x$). The direction of reaction (3) depends on temperature, while the direction of reaction (4) depends both on temperature and catalyst. O-containing compounds (e.g., O-containing compounds formed according to reactions (3)-(4)) are precursors of deep oxidation products, such as CO and $CO_2$, and thus the conversion of methyl radicals via reactions (3)-(4) will lead to $C_{2+}$ selectivity loss.

Furthermore, and without wishing to be limited by theory, as described in reactions (1)-(5), an OCM reaction starts with methyl radical formation, coupling of which leads to the formation of ethane; wherein ethane can be further converted to ethylene through parallel reactions of thermal dehydrogenation and catalytic oxidative dehydrogenation, according to reaction (6). Furthermore, according to reaction (7), ethylene dehydrogenation can produce acetylene. In addition to the oxygenates formed according to reactions (3) and (4), a portion of the $C_{2+}$ products formed (e.g., $C_2H_4$) can also undergo deep oxidation to form CO and $CO_2$. For example, according to reaction (8), ethylene can undergo deep oxidation to CO and $CO_2$. The mechanism of OCM reaction is described in more detail in Lomonosov, V. I. and Sinev, M. Y., Kinetics and Catalysis, 2016, vol.57, pp. 647-676; which is incorporated by reference herein in its entirety.

Furthermore, without wishing to be limited by theory, and as will be appreciated by one of skill in the art, and with the help of this disclosure, when a catalyst (e.g., OCM catalyst) is scaled-up to a pellet with required strength, shape and size, compression is used, wherein the catalyst pellet strength increases with increasing compressing force. Consequently, with increasing pellet strength, the density of the catalyst will increase. With increasing catalyst pellet density, the pore volume of the catalyst is reduced, which in turn enhances mass transfer resistance and enhances the rates of reactions (3), (4), (7), and (8), thereby resulting in a lower performance. The relationship between catalyst density, pore volume and performance in OCM reactions is described in more detail in Lee et al., Fuel, 2013, vol. 106, pp. 851; which is incorporated by reference herein in its entirety.

The multilayer supported OCM catalyst composition as disclosed herein can comprise an alkaline earth metal (A). The alkaline earth metal (A) can be selected from the group consisting of magnesium (Mg), calcium (Ca), strontium (Sr), barium (Ba), and combinations thereof. In an aspect, the alkaline earth metal (A) is strontium (Sr).

The multilayer supported OCM catalyst composition as disclosed herein can comprise a first rare earth element (Z), wherein the first rare earth element (Z) can be selected from the group consisting of lanthanum (La), scandium (Sc), cerium (Ce), praseodymium (Pr), neodymium (Nd), promethium (Pm), samarium (Sm), europium (Eu), gadolinium (Gd), yttrium (Y), terbium (Tb), dysprosium (Dy), holmium (Ho), erbium (Er), thulium (Tm), ytterbium (Yb), lutetium (Lu), and combinations thereof. In an aspect, the first rare earth element (Z) is La. As will be appreciated by one of skill in the art, and with the help of this disclosure, in some aspects, Z can comprise a single rare earth element, such as La. Further, and as will be appreciated by one of skill in the art, and with the help of this disclosure, in some aspects, Z can comprise two or more rare earth elements, such as La, and Nd; or La, Nd, and Pm, as another example; etc.

The multilayer supported OCM catalyst composition as disclosed herein can comprise a second rare earth element (E) and/or a third rare earth element (D), wherein E and D are different. E and D can each independently be selected from the group consisting of La, Sc, Ce, Pr, Nd, Pm, Sm, Eu, Gd, Y, Tb, Dy, Ho, Er, Tm, Yb, Lu, and combinations thereof.

As will be appreciated by one of skill in the art, and with the help of this disclosure, in some aspects, the second rare earth element (E) can comprise a single rare earth element, such as Nd. Further, and as will be appreciated by one of skill in the art, and with the help of this disclosure, in some aspects, E can comprise two or more rare earth elements, such as Yb, and Nd, for example; or Yb, and Tm, as another example; or Yb, Nd, and Tm, as yet another example; etc. As will be appreciated by one of skill in the art, and with the help of this disclosure, in some aspects, the third rare earth element (D) can comprise a single rare earth element, such as Yb. Further, and as will be appreciated by one of skill in the art, and with the help of this disclosure, in some aspects, D can comprise two or more rare earth elements, such as Yb, and Nd, for example; or Yb, Nd, and Pm, as another example; etc.

The multilayer supported OCM catalyst composition as disclosed herein can comprise component (D). As will be appreciated by one of skill in the art, and with the help of this disclosure, D can be either a redox agent or a third rare earth element.

The redox agent (D) can be selected from the group consisting of manganese (Mn), tungsten (W), bismuth (Bi), antimony (Sb), tin (Sn), Ce, Pr, and combinations thereof. A redox agent generally refers to a chemical species that possesses the ability to undergo both an oxidation reaction and a reduction reaction, and such ability usually resides in the chemical species having more than one stable oxidation state other than the oxidation state of zero (0). As will be appreciated by one of skill in the art, and with the help of this disclosure, some rare earth elements, such as Ce and Pr, can also be considered redox agents. Further, as will be appreciated by one of skill in the art, and with the help of this disclosure, when D is Ce and/or Pr, D can be considered either a redox agent or a third rare earth element.

As will be appreciated by one of skill in the art, and with the help of this disclosure, in some aspects, the redox agent (D) can comprise a single element, such as Mn. Further, and as will be appreciated by one of skill in the art, and with the help of this disclosure, in some aspects, the redox agent (D) can comprise two or more compounds, such as Mn, and W, for example; or Mn, W, and Pr, as another example; etc. In some aspects, the redox agent (D) is Mn. In other aspects, the redox agent (D) is W. In an aspect, the redox agent (D) excludes a rare earth element.

In an aspect, the second rare earth element (E) and/or the third rare earth element (D) can be basic (e.g., can exhibit some degree of basicity; can have affinity for hydrogen; can exhibit some degree of affinity for hydrogen). Nonlimiting examples of rare earth elements that can be considered basic for purposes of the disclosure herein include one or more compounds selected from the group consisting of Sc, Ce, Pr, Nd, Pm, Sm, Eu, Gd, Y, Tb, Dy, Ho, Er, Tm, Yb, Lu, and combinations thereof. As will be appreciated by one of skill in the art, and with the help of this disclosure, and without wishing to be limited by theory, the OCM reaction is a multi-step reaction, wherein each step of the OCM reaction could benefit from specific OCM catalytic properties. For example, and without wishing to be limited by theory, an OCM catalyst (e.g., multilayer supported OCM catalyst composition) should exhibit some degree of basicity to abstract a hydrogen from $CH_4$ to form hydroxyl groups [OH] on the catalyst surface, as well as methyl radicals ($CH_3 \cdot$). Further, and without wishing to be limited by theory, an OCM catalyst should exhibit oxidative properties for the OCM catalyst to convert the hydroxyl groups [OH] from the OCM catalyst surface to water, which can allow for the OCM reaction to continue (e.g., propagate). Furthermore, as will be appreciated by one of skill in the art, and with the help of this disclosure, and without wishing to be limited by theory, an OCM catalyst could also benefit from properties like oxygen ion conductivity and proton conductivity, which properties can be critical for the OCM reaction to proceed at a very high rate (e.g., its highest possible rate). Furthermore, an OCM catalyst comprising a single metal might not provide all the necessary properties for an optimum OCM reaction (e.g., best OCM reaction outcome) at the best level, and as such conducting an optimum OCM reaction may require an OCM catalyst with a tailored composition in terms of metals present, as disclosed herein.

In an aspect, the multilayer supported OCM catalyst composition as disclosed herein ($A_aZ_bE_cD_dO_x$/support) comprises a metal oxide component (i.e., $A_aZ_bE_cD_dO_x$) and a support component (i.e., support) wherein the metal oxide component is supported by the support component; wherein at least a portion of the metal oxide component contacts, coats, is embedded in, is supported by, and/or is distributed throughout at least a portion of the support component.

In an aspect, the multilayer supported OCM catalyst composition as disclosed herein ($A_aZ_bE_cD_dO_x$/support) can comprise one or more oxides of A; one or more oxides of Z; one or more oxides of E; one or more oxides of D; or combinations thereof. The multilayer supported OCM catalyst composition as disclosed herein ($A_aZ_bE_cD_dO_x$/support) can comprise one or more oxides of a metal, wherein the metal comprises A, Z, E, and optionally D. In some aspects, the metal oxide component (i.e., $A_aZ_bE_cD_dO_x$) can comprise, consist of, or consist essentially of the one or more oxides of a metal, wherein the metal comprises A, Z, E, and optionally D.

In an aspect, the one or more oxides can be present in metal oxide component (i.e., $A_aZ_bE_cD_dO_x$) in an amount of from about 0.01 wt. % to about 100.0 wt. %, about 0.1 wt. % to about 99.0 wt. %, about 1.0 wt. % to about 95.0 wt. %, about 10.0 wt. % to about 90.0 wt. %, or about 30.0 wt. % to about 70.0 wt. %, based on the total weight of the metal oxide component. As will be appreciated by one of skill in the art, and with the help of this disclosure, a portion of the one or more oxides, in the presence of water, such as atmospheric moisture, can convert to hydroxides, and it is possible that the metal oxide component will comprise some hydroxides, due to exposing the multilayer supported OCM catalyst composition comprising the one or more oxides to water (e.g., atmospheric moisture). Further, as will be appreciated by one of skill in the art, and with the help of this disclosure, a portion of the one or more oxides, in the presence of carbon dioxide ($CO_2$), such as atmospheric $CO_2$, can convert to carbonates, and it is possible that the metal oxide component will comprise some carbonates, due to exposing the metal oxide component comprising the one or more oxides to $CO_2$ (e.g., atmospheric $CO_2$).

The one or more oxides can comprise a single metal oxide, mixtures of single metal oxides, a mixed metal oxide, mixtures of mixed metal oxides, mixtures of single metal oxides and mixed metal oxides, or combinations thereof.

The single metal oxide comprises one metal selected from the group consisting of A, Z, E, and D. A single metal oxide can be characterized by the general formula $M_mO_y$; wherein M is the metal selected from the group consisting of A, Z, E, and D; and wherein m and y are integers from 1 to 7, alternatively from 1 to 5, or alternatively from 1 to 3. A single metal oxide contains one and only one metal cation. Nonlimiting examples of single metal oxides suitable for use in the metal oxide component (i.e., $A_aZ_bE_cD_dO_x$) of the present disclosure include CaO, MgO, SrO, BaO, $La_2O_3$, $Sc_2O_3$, $Y_2O_3$, $CeO_2$, $Ce_2O_3$, $Pr_2O_3$, $PrO_2$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Lu_2O_3$, $Yb_2O_3$, $Tm_2O_3$, $WO_3$, $MnO_2$, $W_2O_3$, $SnO_2$, and the like, or combinations thereof. In an aspect, mixtures of single metal oxides can comprise two or more different single metal oxides, wherein the two or more different single metal oxides have been mixed together to form the mixture of single metal oxides. Mixtures of single metal oxides can comprise two or more different single metal oxides, wherein each single metal oxide can be selected from the group consisting of CaO, MgO, SrO, BaO, $La_2O_3$, $Sc_2O_3$, $Y_2O_3$, $CeO_2$, $Ce_2O_3$, $Pr_2O_3$, $PrO_2$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Lu_2O_3$, $Yb_2O_3$, $Tm_2O_3$, $WO_3$, $MnO_2$, $W_2O_3$, and $SnO_2$. Nonlimiting examples of mixtures of single metal oxides suitable for use in the metal oxide component (i.e., $A_aZ_bE_cD_dO_x$) of the present disclosure include SrO—$La_2O_3$, SrO—MgO—$La_2O_3$, SrO—$Yb_2O_3$—$La_2O_3$, SrO—$Er_2O_3$—$La_2O_3$, SrO—$CeO_2$—$La_2O_3$, SrO—$MnO_2$—$La_2O_3$, SrO—$WO_3$—$W_2O_3$—$La_2O_3$, SrO—$WO_3$—$Tm_2O_3$—$La_2O_3$, SrO—$WO_3$—$Tm_2O_3$—$La_2O_3$, SrO—BaO—$CeO_2$—$Er_2O_3$—$La_2O_3$, SrO—$CeO_2$—$Ce_2O_3$—$Er_2O_3$—$La_2O_3$, SrO—BaO—$WO_3$—$W_2O_3$—$La_2O_3$, SrO—BaO—$Sm_2O_3$—$WO_3$—$W_2O_3$—$La_2O_3$, SrO—MgO—$CeO_2$—$Ce_2O_3$—$WO_3$—$W_2O_3$—$La_2O_3$, SrO—CaO—$PrO_2$—$Pr_2O_3$—MnO—$Mn_2O_3$—$La_2O_3$, and the like, or combinations thereof.

The mixed metal oxide comprises two or more different metals, wherein each metal can be independently selected from the group consisting of A, Z, E, and D. A mixed metal oxide can be characterized by the general formula $M^1_{m1}M^2_{m2}O_y$; wherein $M^1$ and $M^2$ are metals; wherein each of the $M^1$ and $M^2$ can be independently selected from the group consisting of A, Z, E, and D; and wherein m1, m2 and y are integers from 1 to 15, alternatively from 1 to 10, or alternatively from 1 to 7. In some aspects, $M^1$ and $M^2$ can be metal cations of different chemical elements, for example $M^1$ can be a lanthanum cation and $M^2$ can be a strontium cation. In other embodiments, $M^1$ and $M^2$ can be different cations of the same chemical element, wherein $M^1$ and $M^2$ can have different oxidation states. For example, the mixed metal oxide can comprise $Mn_3O_4$, wherein $M^1$ can be a Mn (II) cation and $M^2$ can be a Mn (III) cation. Nonlimiting examples of mixed metal oxides suitable for use in the metal oxide component (i.e., $A_aZ_bE_cD_dO_x$) of the present disclosure include La/SrO; $LaYbO_3$; $SrYb_2O_4$; $Sr_2CeO_4$; $Mn_3O_4$; La/MgO; $Sm_2Ce_2O_7$; $Er_2Ce_2O_7$; $CaTm_2O_4$; $MgYb_2O_4$; $SrCe_{(1-y)}Yb_yO_3$, wherein y can be from about 0.01 to about 0.99; and the like; or combinations thereof. Mixtures of mixed metal oxides can comprise two or more different mixed metal oxides, wherein the two or more different mixed metal oxides have been mixed together to form the mixture of mixed metal oxides. Mixtures of mixed metal oxides can comprise two or more different mixed metal oxides, such as La/SrO; $LaYbO_3$; $SrYb_2O_4$; $Sr_2CeO_4$; $Mn_3O_4$; La/MgO; $Sm_2Ce_2O_7$; $Er_2Ce_2O_7$; $CaTm_2O_4$; $MgYb_2O_4$; $SrCe_{(1-y)}Yb_yO_3$, wherein y can be about 0.01 to about 0.99; and the like; or combinations thereof.

Mixtures of single metal oxides and mixed metal oxides can comprise at least one single metal oxide and at least one mixed metal oxide, with the at least one single metal oxide and the at least one mixed metal oxide have been mixed together to form the mixture of single metal oxides and mixed metal oxides.

In an aspect, the multilayer supported OCM catalyst composition as disclosed herein comprises a support, wherein the metal oxide component (i.e., $A_aZ_bE_cD_dO_x$) described herein is physically or structurally supported by the support component (i.e., support) such that the metal oxide component is provided with additional structural and/or mechanical strength (e.g., improved crush strength) in comparison to unsupported metal oxide component. In an aspect, the multilayer supported OCM catalyst composition comprises a metal oxide component supported by a support component, wherein at least a portion of the metal oxide component contacts, coats, is embedded in, is supported by, and/or is distributed throughout at least a portion of the support component. For purposes of the disclosure herein the terms "support" and "support component" refer to the material that provides additional structural and/or mechanical strength to the metal oxide component and can be used interchangeably. In an aspect, the support can be in the form of powders, particles, pellets, monoliths, foams, honeycombs, and the like, or combinations thereof. Nonlimiting examples of support particle shapes include cylindrical, discoidal, spherical, tabular, ellipsoidal, equant, irregular, cubic, acicular, and the like, or combinations thereof.

As will be appreciated by one of skill in the art, and with the help of this disclosure, the support can be purchased or can be prepared by using any suitable methodology, such as for example precipitation/co-precipitation, sol-gel techniques, templates/surface derivatized metal oxides synthesis, solid-state synthesis of mixed metal oxides, microemulsion techniques, solvothermal techniques, sonochemical techniques, combustion synthesis, etc.

In an aspect, the multilayer supported OCM catalyst composition as disclosed herein can further comprise a porous support. As will be appreciated by one of skill in the art, and with the help of this disclosure, a porous material (e.g., porous support) can provide for an enhanced surface area of contact between the metal oxide component and a reactant mixture, which in turn would result in a higher $CH_4$ conversion to $CH_3$.

The support can have a surface area in a range of from greater than 0 m$^2$/g and less than about 20.0 m$^2$/g, alternatively in a range of from greater than 0 m$^2$/g and less than about 10.0 m$^2$/g, or alternatively in a range of from greater than 0 m$^2$/g and less than about 5.0 m$^2$/g, as determined by measuring nitrogen adsorption according to the Brunauer, Emmett and Teller (BET) method. The support can have a total pore volume of from about 0.1 cc/g to about 1.0 cc/g, about 0.15 cc/g to about 0.9 cc/g, or about 0.2 cc/g to about 0.8 cc/g, as determined by measuring nitrogen adsorption according to the BET method. The support can have a pore size distribution of from about 0.01 microns to about 500 microns, about 0.1 microns to about 300 microns, or about 0.5 microns to about 200 microns, as determined by measuring nitrogen adsorption according to the BET method.

Nonlimiting examples of a support suitable for use in the present disclosure include alumina ($Al_2O_3$), silica ($SiO_2$), silica ($SiO_2$)-alumina ($Al_2O_3$), silicon carbide (SiC), zirconia ($ZrO_2$), titania ($TiO_2$), magnesium oxide (MgO), zeolites, transition metal oxides, alkali metal oxides, alkaline earth metal oxides, lanthanide oxides, actinide oxides, carbon, and the like, or combinations thereof. In an aspect, the support is a silica-alumina ($SiO_2$—$Al_2O_3$). In an aspect, the support is alumina ($Al_2O_3$).

In an aspect, the multilayer supported OCM catalyst composition as disclosed herein can comprise a zeolitic support. For purposes of the disclosure herein the term "zeolitic support(s)" includes zeolitic structures, zeolitic frameworks, aluminosilicates, aluminosilicates structures, aluminosilicates frameworks, zeolite-type materials, zeolite-type structures, zeolite-type frameworks, molecular sieves, silicoaluminophosphates, silicoaluminophosphates structures, silicoaluminophosphates frameworks, aluminophosphates, aluminophosphates structures, aluminophosphates frameworks, and the like, or combinations thereof. Further, for purposes of the disclosure herein, zeolitic structures, zeolitic frameworks, aluminosilicates, aluminosilicates structures, aluminosilicates frameworks, zeolite-type materials, zeolite-type structures, zeolite-type frameworks, molecular sieves, silicoaluminophosphates, silicoaluminophosphates structures, silicoaluminophosphates frameworks, aluminophosphates, aluminophosphates structures, aluminophosphates frameworks, and the like, or combinations thereof are referred to herein collectively as "zeolites."

The multilayer supported OCM catalyst composition (comprising a support component and a metal oxide component of the type described herein) can have any suitable desired particle specifications (e.g., crush strength, pressure drop across a catalyst bed, etc.), for example as required by a specific application. For example, the multilayer supported OCM catalyst composition can be characterized by a size suitable for use in a particular reactor (e.g., an OCM reactor having a particular catalyst bed configuration). As will be appreciated by one of skill in the art, and with the help of this disclosure, the size of the multilayer supported OCM catalyst composition can be determined for a particular application to achieve the best performance for the OCM reaction (e.g., desired conversion, desired selectivity, pressure drop, residence time, etc.).

The multilayer supported OCM catalyst composition as disclosed herein can comprise a support in an amount of from about 5 wt. % to about 95 wt. %, about 25 wt. % to about 75 wt. %, or about 35 wt. % to about 65 wt. %, based on the total weight of the multilayer supported OCM catalyst composition. As will be appreciated by one of skill in the art, and with the help of this disclosure, the amount of the metal oxide component (i.e., $A_aZ_bE_cD_dO_x$) on the support, and consequently the amount of support in the catalyst composition (e.g., multilayer supported OCM catalyst composition), can depend on the catalytic activity of the metal oxide component.

In alternative aspects, the multilayer supported OCM catalyst composition can have a weight ratio of the metal oxide component (i.e., $A_aZ_bE_cD_dO_x$) to the support component of from about 0.01 to about 5.0, about 0.05 to about 2.0, or about 0.1 to about 1.0.

The multilayer supported OCM catalyst composition as disclosed herein can have a density of from about 0.3 g/cc to about 4.5 g/cc, about 0.5 g/cc to about 3.0 g/cc, or about 0.8 g/cc to about 2.0 g/cc. The multilayer supported OCM catalyst composition as disclosed herein can have a crush strength of from about 1 N to about 800 N, about 2 N to about 400 N, or about 3 N to about 100 N.

In an aspect, the metal oxide component (i.e., $A_aZ_bE_cD_dO_x$) can be characterized by a thickness of from about 0.005 μm to about 250 μm, about 0.02 μm to about 200 μm, or about 0.2 μm to about 150 μm. As will be appreciated by one of skill in the art, and with the help of this disclosure, the thickness of the metal oxide component refers to the overall thickness of the metal oxide component, and it accounts for and encompasses a thickness of the first single oxide layer, a thickness of the one or more mixed oxide layers, and a thickness of the second single oxide layer (when present). In other words, the thickness of the metal oxide component is the sum of the thickness of the first single oxide layer, the thickness of the one or more mixed oxide layers, and the thickness of the second single oxide layer (when present).

In an aspect, the first single oxide layer contacts the support and the one or more mixed oxide layers; wherein the first single oxide layer is characterized by the general formula $Z_{b1}O_{x1}$, wherein b1 is from about 0.1 to about 10.0, alternatively from about 0.3 to about 10.0, alternatively from about 0.5 to about 8, or alternatively from about 1 to about 5; and wherein x1 balances the oxidation states. The support is characterized by an external surface, wherein the first single oxide layer contacts at least a portion of the external surface of the support.

In some aspects, the first single oxide layer can contact equal to or greater than about 60%, about 70%, about 80%, about 90%, about 95%, about 99%, or alternatively about 100% of the external surface of the support.

In some aspects, the first single oxide layer substantially coats the entire external surface of the support (e.g., about 100% of the external surface of the support). In aspects where the first single oxide layer contacts about 100% of the external surface of the support (e.g., the first single oxide layer fully coats the entire external surface of the support), the first single oxide layer is a continuous layer.

In aspects where the first single oxide layer contacts less than about 100% of the external surface of the support, the first single oxide layer may be a continuous layer (wherein all portions of the first single oxide layer are connected to each other) or a discontinuous layer (wherein some portions of the first single oxide layer are not connected to each other, do not contact each other, etc.). Discontinuous layers, such as a discontinuous first single oxide layer, may comprise isolated layer regions or islands.

In an aspect, the first single oxide layer can be characterized by a thickness of from about 0.001 μm to about 100 μm, about 0.01 μm to about 50 μm, or about 0.05 μm to about 10 μm.

In an aspect, the first single oxide layer characterized by the general formula $Z_{b1}O_{x1}$ comprises a single metal oxide or mixtures of single metal oxides. Nonlimiting examples of single metal oxides suitable for use in the first single oxide layer include $La_2O_3$, $Sc_2O_3$, $Y_2O_3$, $CeO_2$, $Ce_2O_3$, $Pr_2O_3$, $PrO_2$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Lu_2O_3$, $Yb_2O_3$, $Tm_2O_3$, and the like, or combinations thereof. In some aspects, the first single oxide layer can comprise, consist of, or consist essentially of $La_2O_3$.

In some aspects, the first single oxide layer can comprise, consist of, or consist essentially of one or more single metal oxides, wherein the metal is Z. As will be appreciated by one of skill in the art, and with the help of this disclosure, a portion of the one or more single metal oxides of the first single oxide layer, in the presence of water, such as atmospheric moisture, can convert to hydroxides; and/or a portion of the one or more single metal oxides of the first single oxide layer, in the presence of $CO_2$, such as atmospheric $CO_2$, can convert to carbonates, as previously described herein.

In an aspect, the first single oxide layer can be present in the metal oxide component in an amount of from about 0.1 wt. % to about 50 wt. %, about 1.0 wt. % to about 40 wt. %, or about 5 wt. % to about 30 wt. %, based on the total weight of the metal oxide component.

In an aspect, the one or more mixed oxide layers contacts the first single oxide layer and optionally the second single oxide layer (when present); wherein the one or more mixed oxide layers is characterized by the general formula $A_{a2}Z_{b2}E_{c2}D_{d2}O_{x2}$, wherein a2 is 1.0; wherein b2 is from about 0.1 to about 10.0, about 0.3 to about 10.0, about 0.5 to about 8, or about 1 to about 5; wherein c2 is from about 0.1 to about 10.0, about 0.1 to about 8, or about 0.5 to about 5; wherein d2 is from about 0 to about 10.0, about 0.1 to about 8, or about 0.5 to about 5; wherein x2 balances the oxidation states; and wherein the general formula $A_aZ_bE_cD_dO_x$ and the general formula $A_{a2}Z_{b2}E_{c2}D_{d2}O_{x2}$ are different. As will be appreciated by one of skill in the art, and with the help of this disclosure, the one or more mixed oxide layers characterized by the general formula $A_{a2}Z_{b2}E_{c2}D_{d2}O_{x2}$ contributes to the general formula $A_aZ_bE_cD_dO_x$ of the multilayer supported OCM catalyst composition along with the first single oxide layer characterized by the general formula $Z_{b1}O_{x1}$, and optionally the second single oxide layer characterized by the general formula AO. The first single oxide layer can be characterized by a first single oxide layer inner external surface and by a first single oxide layer outer external surface, wherein the first single oxide layer inner external surface spatially opposes the first single oxide layer outer external surface, wherein the first single oxide layer inner external surface contacts the external surface of the support, and wherein the first single oxide layer outer external surface contacts the one or more mixed oxide layers.

In aspects where the first single oxide layer contacts less than about 100% of the external surface of the support, a portion of the one or more mixed oxide layers may further contact the external surface of the support.

In aspects where the first single oxide layer contacts about 100% of the external surface of the support (e.g., the first single oxide layer fully coats the entire external surface of the support), the one or more mixed oxide layers do not contact any portion of the external surface of the support.

In some aspects, the one or more mixed oxide layers can contact from about 40% to about 99%, about 50% to about 95%, about 55% to about 90%, about 60% to about 85%, or about 65% to about 80% of the first single oxide layer outer external surface. The one or more mixed oxide layers may be continuous layers (wherein all portions of the one or more mixed oxide layers are connected to each other) or a discontinuous layer (wherein some portions of the one or more mixed oxide layers are not connected to each other, do not contact each other, etc.). Discontinuous layers, such as a discontinuous one or more mixed oxide layers, may comprise isolated layer regions or islands.

The one or more mixed oxide layers can be characterized by a thickness of from about 0.002 μm to about 250 μm, about 0.02 μm to about 200 μm, or a about 0.2 μm to about 150 μm. The one or more mixed oxide layers can comprise from about 1 to about 10, about 2 to about 7, or about 3 to about 5 layers (e.g., mixed oxide layers). In an aspect, each layer of the one or more mixed oxide layers can be characterized by a thickness of from about 0.001 μm to about 200 μm, about 0.01 μm to about 150 μm, or about 0.02 μm to about 100 μm.

In some aspects where the multilayer supported OCM catalyst composition comprises more than 1 layer, all layers of the one or more mixed oxide layers can be characterized by the same composition (i.e., a composition characterized by the general formula $A_{a2}Z_{b2}E_{c2}D_{d2}O_{x2}$). In other words, the composition of each layer of the one or more mixed oxide layers is the same as the overall composition of the one or more mixed oxide layers.

In some aspects where the multilayer supported OCM catalyst composition comprises more than 1 layer, at least 2 layers of the one or more mixed oxide layers can be characterized by compositions different from each other. In other words, the composition of the at least 2 layers of the one or more mixed oxide layers characterized by compositions different from each other is different from the overall composition of the one or more mixed oxide layers. For example, a layer of the one or more mixed oxide layers can comprise oxides of Sr, La, and Yb, while another layer of the one or more mixed oxide layers can comprise oxides of Sr, Yb, and Nd; wherein the overall one or more mixed oxide layers can comprise oxides of Sr, La, Yb, and Nd.

In an aspect, the one or more mixed oxide layers characterized by the general formula $A_{a2}Z_{b2}E_{c2}D_{d2}O_{x2}$ comprises one or more oxides of A; one or more oxides of Z; one or more oxides of E; one or more oxides of D; or combinations thereof. The one or more mixed oxide layers characterized by the general formula $A_{a2}Z_{b2}E_{c2}D_{d2}O_{x2}$ can comprise one or more oxides of a metal, wherein the metal comprises A, Z, E, and optionally D. In some aspects, the one or more mixed oxide layers characterized by the general formula $A_{a2}Z_{b2}E_{c2}D_{d2}O_{x2}$ can comprise, consist of, or consist essentially of the one or more oxides of a metal, wherein the metal comprises A, Z, E, and optionally D. The one or more oxides present in the one or more mixed oxide layers characterized by the general formula $A_{a2}Z_{b2}E_{c2}D_{d2}O_{x2}$ can comprise any suitable metal oxide disclosed herein (e.g., a single metal oxide, mixtures of single metal oxides, a mixed metal oxide, mixtures of mixed metal oxides, mixtures of single metal oxides and mixed metal oxides, or combinations thereof).

In some aspects, the one or more mixed oxide layers can have the general formula $Sr_{a2}La_{b2}Y_{c2}Nd_{d2}O_{x2}$; wherein a2 is 1.0; wherein b2 is about 0.1 to about 10.0; wherein c2 is about 0.1 to about 10.0; wherein d2 is about 0 to about 10.0; and wherein x2 balances the oxidation states.

As will be appreciated by one of skill in the art, and with the help of this disclosure, a portion of the one or more oxides present in the one or more mixed oxide layers characterized by the general formula $A_{a2}Z_{b2}E_{c2}D_{d2}O_{x2}$, in the presence of water, such as atmospheric moisture, can convert to hydroxides; and/or a portion of the one or more oxides present in the one or more mixed oxide layers characterized by the general formula $A_{a2}Z_{b2}E_{c2}D_{d2}O_{x2}$, in the presence of $CO_2$, such as $CO_2$, can convert to carbonates, and it is possible that the one or more mixed oxide layers will comprise some carbonates; as previously described herein.

In an aspect, the one or more mixed oxide layers can be present in the metal oxide component in an amount of from about 50.0 wt. % to about 99.9 wt. %, about 60.0 wt. % to about 99.0 wt. %, or about 70.0 wt. % to about 95.0 wt. %, based on the total weight of the metal oxide component.

In an aspect, the second single oxide layer, when present, contacts the one or more mixed oxide layers and optionally the first single oxide layer, wherein the second single oxide layer is characterized by the general formula AO. The one or more mixed oxide layers can be characterized by a one or more mixed oxide layers inner external surface and by a one or more mixed oxide layers outer external surface, wherein the one or more mixed oxide layers inner external surface spatially opposes the one or more mixed oxide layers outer external surface, wherein the one or more mixed oxide layers inner external surface contacts the first single oxide layer outer external surface and optionally the external surface of the support, and wherein the one or more mixed oxide layers outer external surface contacts the second single oxide layer. In some aspects, a portion of the second single oxide layer may further contact the first single oxide layer outer external surface and/or the external surface of the support.

In some aspects, the second single oxide layer can contact from about 5% to about 50%, about 7.5% to about 40%, about 10% to about 35%, about 12.5% to about 30%, or about 15% to about 25% of the one or more mixed oxide layers outer external surface.

The second single oxide layer may be a continuous layer (wherein all portions of the second single oxide layer are connected to each other) or a discontinuous layer (wherein some portions of the second single oxide layer are not connected to each other, do not contact each other, etc.). Discontinuous layers, such as a discontinuous second single oxide layer, may comprise isolated layer regions or islands.

In an aspect, the second single oxide layer can be characterized by a thickness of from about 0.001 μm to about 50 μm, about 0.01 μm to about 10 μm, or about 0.1 μm to about 5 μm.

In an aspect, the second single oxide layer characterized by the general formula AO comprises a single alkaline earth metal oxide or mixtures of single alkaline earth metal oxides. Nonlimiting examples of single alkaline earth metal oxides suitable for use in the second single oxide layer include CaO, MgO, SrO, BaO, and the like, or combinations thereof. In some aspects, the second single oxide layer can comprise, consist of, or consist essentially of SrO.

In some aspects, the first single oxide layer can comprise, consist of, or consist essentially of one or more single alkaline earth metal (A) oxides. As will be appreciated by one of skill in the art, and with the help of this disclosure, a portion of the one or more single alkaline earth metal oxides of the second single oxide layer, in the presence of water (e.g., atmospheric moisture), can convert to hydroxides; and/or a portion of the one or more single alkaline earth metal oxides of the second single oxide layer, in the presence of $CO_2$, such as atmospheric $CO_2$, can convert to carbonates; as previously described herein.

In an aspect, the second single oxide layer can be present in the metal oxide component in an amount of from about 0.1 wt. % to about 20.0 wt. %, about 1.0 wt. % to about 15.0 wt. %, or about 2.0 wt. % to about 10.0 wt. %, based on the total weight of the metal oxide component.

A multilayer supported OCM catalyst composition as disclosed herein can be made by using any suitable methodology. In an aspect, the multilayer supported OCM catalyst is prepared by contacting a support with a metal oxide component (i.e., $A_aZ_bE_cD_dO_x$) of the type described herein. In an aspect, the multilayer supported OCM catalyst is prepared by contacting a support with one or more components of a metal oxide component of the type described herein. In an aspect, the multilayer supported OCM catalyst is prepared by contacting a support with one or more components (e.g., one or more metal compounds in solution such as an OCM catalyst precursor mixture) of a metal oxide component of the type described herein.

In an aspect, a method of making a multilayer supported OCM catalyst composition as disclosed herein can comprise a step of contacting a support with a first OCM catalyst precursor mixture to form a first supported OCM catalyst precursor, wherein the first OCM catalyst precursor mixture comprises one or more compounds comprising a first rare earth element cation.

In an aspect, a method of making a multilayer supported OCM catalyst composition as disclosed herein can comprise a step of forming or otherwise obtaining a first OCM catalyst precursor mixture (e.g., an aqueous solution); wherein the first OCM catalyst precursor mixture comprises one or more compounds comprising a first rare earth element cation. The one or more compounds comprising a first rare earth element cation can comprise a first rare earth element nitrate, a first rare earth element oxide, a first rare earth element hydroxide, a first rare earth element chloride, a first rare earth element acetate, a first rare earth element carbonate, and the like, or combinations thereof.

In some aspects, the first OCM catalyst precursor mixture can be formed in the presence of water, for example by contacting water or any suitable aqueous medium with one or more compounds comprising a first rare earth element (Z) cation. The first OCM catalyst precursor mixture comprises water.

In other aspects, the first OCM catalyst precursor mixture can be formed in the absence of water (e.g., substantial absence of water; without adding water, etc.), for example by contacting the compounds comprising a first rare earth element (Z) cation with each other (when more than one compound comprising a Z cation is used). As will be appreciated by one of skill in the art, and with the help of this disclosure, whether water is used or not for forming the first OCM catalyst precursor mixture, the first OCM catalyst precursor mixture can be further subjected to a step of drying and/or calcining as disclosed herein. Without wishing to be limited by theory, some of the compounds comprising a first rare earth element cation can be insoluble in water, or only partially soluble in water (e.g., lanthanum oxide, ytterbium oxide, strontium carbonate, neodymium oxide, etc.); and in such instances, these compounds cannot be solubilized in water, but rather mixed as dry materials, or with little water as to (e.g., an amount of water effective to) form a paste (e.g., homogeneous mixture), and the paste (e.g., homogeneous mixture) may be further contacted with the support (e.g., mixed together). Further, and as will be appreciated by one of skill in the art, and with the help of this disclosure, even when the first OCM catalyst precursor mixture is formed without water addition, the first OCM catalyst precursor mixture can contain a small amount of water (e.g., from atmospheric moisture).

In an aspect, the step of forming the first OCM catalyst precursor mixture can comprise solubilizing the one or more compounds comprising a first rare earth element cation in an aqueous medium to form the first OCM catalyst precursor mixture (e.g., a first OCM catalyst precursor aqueous solution). The aqueous medium can be water, or an aqueous solution. The first OCM catalyst precursor aqueous solution can be formed by dissolving the one or more compounds comprising a first rare earth element cation in water or any suitable aqueous medium. As will be appreciated by one of skill in the art, and with the help of this disclosure, when more than one compound comprising a first rare earth element cation is used, the compounds comprising a first rare earth element cation can be dissolved in an aqueous medium in any suitable order. In some aspects, the compounds comprising a first rare earth element cation can be first mixed together and then dissolved in an aqueous medium.

In an aspect, a method of making the multilayer supported OCM catalyst composition comprises contacting at least a portion of the first OCM catalyst precursor mixture with a support such that the first OCM catalyst precursor mixture is supported by the support to form an impregnated support, and this may also be referred to as metalizing the support. In an aspect, a method of making the multilayer supported OCM catalyst comprises contacting at least a portion of the first OCM catalyst precursor mixture with a support such that at least a portion of the first OCM catalyst precursor mixture contacts, coats, is embedded in, is supported by, and/or is distributed throughout at least a portion of the support to form a first impregnated support.

In an aspect, a step of forming a first supported OCM catalyst precursor comprises contacting a first OCM catalyst precursor aqueous solution with a support such that the first OCM catalyst precursor aqueous solution is supported by the support to form a first impregnated support. In an aspect, a step of forming a first supported OCM catalyst precursor comprises contacting a first OCM catalyst precursor aqueous solution with a porous support (e.g., alumina-silica) such that at least a portion of the first OCM catalyst precursor aqueous solution contacts, coats, is embedded in, is supported by, and/or is distributed throughout at least a portion of the porous support to form a first impregnated support. The first OCM catalyst precursor aqueous solution can be contacted with the support according to any suitable procedure, including but not limited to incipient wetness impregnation, wet impregnation, soaking, ion exchange, coating (dip or spray), or chemical deposition.

In an aspect, a step of forming a first supported OCM catalyst precursor comprises contacting a first OCM catalyst precursor aqueous solution with a porous support (e.g., alumina-silica), wherein the contacting is performed via incipient wetness impregnation (also called capillary impregnation or dry impregnation) with an aqueous solution comprising the one or more compounds comprising a first rare earth element cation to form a first impregnated support. With incipient wetness impregnation, capillary action draws the solution into the pores, and thus an amount of the first OCM catalyst precursor aqueous solution added to the support is typically equal to or less than the total pore volume of the support. Where the amount of first OCM catalyst precursor aqueous solution added to the support is less than the total pore volume of the support, multiple contacting steps can be used such that the total amount of first OCM catalyst precursor aqueous solution added to the support is about equal to the total pore volume of the support. The first OCM catalyst precursor aqueous solution added in excess of the support pore volume may cause the solution transport to change from a capillary action process to a diffusion process, which can slow the impregnation process. The loading of the first OCM catalyst precursor aqueous solution can be controlled by the concentration of metal ions in solution, which means that the support external surface does not play an important role, but merely acts as a physical support. The maximum loading of the first OCM catalyst precursor aqueous solution into the support can be limited by the solubility of the individual components of the first OCM catalyst precursor aqueous solution in the solution (e.g., in water). The first impregnated support can then be dried and calcined to drive off the volatile components within the solution, depositing the one or more compounds comprising a first rare earth element cation on the external surface of the support (e.g., outer surface and surface of pores).

In an aspect, the step of forming the first OCM catalyst precursor mixture can comprise drying at least a portion of the first OCM catalyst precursor at a temperature of equal to or greater than about 75° C., about 90° C., about 100° C., about 110° C., or about 125° C., alternatively from about 75° C. to about 400° C., about 80° C. to about 400° C., about 100° C. to about 400° C., about 125° C. to about 400° C., about 75° C. to about 200° C., about 80° C. to about 200° C., about 100° C. to about 200° C., or about 125° C. to about 200° C., to yield a dried first impregnated support. The first OCM catalyst precursor can be dried for a time period of equal to or greater than about 2 hours (h), about 4 h, about 8 h, or about 12 h, to yield the dried first impregnated support.

In an aspect, a method of making a multilayer supported OCM catalyst composition as disclosed herein can comprise a step of calcining at least a portion of the first supported OCM catalyst precursor (e.g., first impregnated support, dried first impregnated support) to form a first calcined supported OCM catalyst precursor comprising the support and a first single oxide layer, wherein the first single oxide layer contacts the support, wherein the first single oxide layer is characterized by the general formula $Z_{b1}O_{x1}$, and wherein b1 is from about 0.1 to about 10.0; and wherein x1 balances the oxidation states.

The first supported OCM catalyst precursor (e.g., first impregnated support, dried first impregnated support) can be calcined at a temperature of equal to or greater than about 500° C., about 550° C., about 600° C., about 650° C., about 700° C., about 750° C., about 800° C., about 850° C., or about 900° C., alternatively from about 500° C. to about 1,100° C., about 550° C. to about 1,100° C., about 600° C. to about 1,100° C., about 650° C. to about 1,100° C., about 700° C. to about 1,100° C., about 750° C. to about 1,100° C., about 800° C. to about 1,100° C., about 850° C. to about 1,100° C., or about 900° C. to about 1,100° C., to yield the first calcined supported OCM catalyst precursor. The first supported OCM catalyst precursor (e.g., first impregnated support, dried first impregnated support) can be calcined for a time period of equal to or greater than about 2 h, about 4 h, or about 6 h.

In some aspects, at least a portion of the first supported OCM catalyst precursor (e.g., first impregnated support, dried first impregnated support) can be calcined in an oxidizing atmosphere (e.g., in an atmosphere comprising oxygen, for example in air) to form the first calcined supported OCM catalyst precursor. Without wishing to be limited by theory, the oxygen in the first calcined supported OCM catalyst precursor having the first single oxide layer characterized by the general formula $Z_{b1}O_{x1}$ can originate in the oxidizing atmosphere used for calcining the first supported OCM catalyst precursor. Further, without wishing to be limited by theory, the oxygen in the first calcined supported OCM catalyst precursor having the first single oxide layer characterized by the general formula $Z_{b1}O_{x1}$ can originate in the one or more compounds comprising a first rare earth element cation used for forming the first single oxide layer, provided that at least one of these compounds comprises oxygen in its formula, as is the case with nitrates, oxides, hydroxides, acetates, carbonates, etc.

A method of making a multilayer supported OCM catalyst composition as disclosed herein can comprise a step of contacting at least a portion of the first calcined supported OCM catalyst precursor with a second OCM catalyst precursor mixture to form a second supported OCM catalyst precursor, wherein the second OCM catalyst precursor mixture comprises one or more compounds comprising an alkaline earth metal (A) cation, one or more compounds comprising a first rare earth element (Z) cation, one or more compounds comprising a second rare earth element (E) cation, and one or more compounds comprising a redox agent cation or a third rare earth element (D) cation; wherein the first rare earth element cation, the second rare earth element cation, and the third rare earth element cation, when present, are not the same (i.e., are different). The second OCM catalyst precursor mixture is characterized by a molar ratio of first rare earth element to alkaline earth metal of b2:1, wherein b2 is about 0.1 to about 10.0, about 0.3 to about 10.0, about 0.5 to about 8, or about 1 to about 5. The second OCM catalyst precursor mixture is characterized by a molar ratio of second rare earth element to alkaline earth metal of c2:1, wherein c2 is from about 0.1 to about 10.0, about 0.1 to about 8, or about 0.5 to about 5. The second OCM catalyst precursor mixture is characterized by a molar ratio of redox agent or third rare earth element to alkaline earth metal of d2:1, wherein d2 is from about 0 to about 10.0, about 0.1 to about 8, or about 0.5 to about 5.

The one or more compounds comprising an alkaline earth metal cation can comprise an alkaline earth metal nitrate, an alkaline earth metal oxide, an alkaline earth metal hydroxide, an alkaline earth metal chloride, an alkaline earth metal acetate, an alkaline earth metal carbonate, and the like, or combinations thereof. The one or more compounds comprising a first rare earth element cation can comprise a first rare earth element nitrate, a first rare earth element oxide, a first rare earth element hydroxide, a first rare earth element chloride, a first rare earth element acetate, a first rare earth element carbonate, and the like, or combinations thereof. The one or more compounds comprising a second rare earth element cation can comprise a second rare earth element nitrate, a second rare earth element oxide, a second rare earth element hydroxide, a second rare earth element chloride, a second rare earth element acetate, a second rare earth element carbonate, and the like, or combinations thereof. The one or more compounds comprising a redox agent cation can comprise a redox agent nitrate, a redox agent oxide, a redox agent hydroxide, a redox agent chloride, a redox agent acetate, a redox agent carbonate, and the like, or combinations thereof. The one or more compounds comprising a third rare earth element cation can comprise a third rare earth element nitrate, a third rare earth element oxide, a third rare earth element hydroxide, a third rare earth element chloride, a third rare earth element acetate, a third rare earth element carbonate, and the like, or combinations thereof.

In some aspects, the second OCM catalyst precursor mixture can be formed in the presence of water, for example by contacting water or any suitable aqueous medium with one or more compounds comprising an alkaline earth metal (A) cation, one or more compounds comprising a first rare earth element (Z) cation, one or more compounds comprising a second rare earth element (E) cation, and optionally one or more compounds comprising a redox agent or a third rare earth element (D) cation. In such aspects, the second OCM catalyst precursor mixture comprises water.

In other aspects, the second OCM catalyst precursor mixture can be formed in the absence of water (e.g., substantial absence of water; without adding water, etc.), as previously described herein for forming the first OCM catalyst precursor mixture in the absence of water.

In an aspect, a step of forming the second OCM catalyst precursor mixture can comprise solubilizing the one or more compounds comprising an alkaline earth metal cation, one or more compounds comprising a first rare earth element cation, one or more compounds comprising a second rare earth element cation, and one or more compounds comprising a redox agent cation or a third rare earth element cation in an aqueous medium to form to form the second OCM catalyst precursor mixture (e.g., a second OCM catalyst precursor aqueous solution). The aqueous medium can be water, or an aqueous solution. The second OCM catalyst precursor aqueous solution can be formed by dissolving the one or more compounds comprising an alkaline earth metal cation, one or more compounds comprising a first rare earth element cation, one or more compounds comprising a second rare earth element cation, one or more compounds comprising a redox agent cation or a third rare earth element cation, or combinations thereof, in water or any suitable aqueous medium. As will be appreciated by one of skill in the art, and with the help of this disclosure, the one or more compounds comprising an alkaline earth metal cation, one or more compounds comprising a first rare earth element cation, one or more compounds comprising a second rare earth element cation, and one or more compounds comprising a redox agent cation or a third rare earth element cation can be dissolved in an aqueous medium in any suitable order. In some aspects, the one or more compounds comprising an alkaline earth metal cation, one or more compounds comprising a first rare earth element cation, one or more compounds comprising a second rare earth element cation, and one or more compounds comprising a redox agent cation or a third rare earth element cation can be first mixed together and then dissolved in an aqueous medium.

In an aspect, a method of making a multilayer supported OCM catalyst composition as disclosed herein can comprise a step of contacting at least a portion of the first calcined supported OCM catalyst precursor with a second OCM catalyst precursor mixture such that the second OCM catalyst precursor mixture is supported by the first calcined supported OCM catalyst precursor to form a second impregnated support. In an aspect, a method of making a multilayer supported OCM catalyst composition as disclosed herein can comprise a step of contacting at least a portion of the first calcined supported OCM catalyst precursor with a second OCM catalyst precursor mixture such that the second OCM catalyst precursor mixture contacts, coats, etc. the first single oxide layer outer external surface as described herein.

In an aspect, a method of making a multilayer supported OCM catalyst composition as disclosed herein comprises contacting a second OCM catalyst precursor aqueous solution with at least a portion of the first calcined supported OCM catalyst precursor comprising the support to form the second impregnated support. In an aspect, a method of making a multilayer supported OCM catalyst composition as disclosed herein comprises contacting a second OCM catalyst precursor aqueous solution with the first calcined supported OCM catalyst precursor comprising a porous support, for example according to any suitable procedure, including but not limited to incipient wetness impregnation, wet impregnation, soaking, ion exchange, coating (dip or spray), or chemical deposition.

In an aspect, a step of forming the second OCM catalyst precursor mixture can comprises contacting a second OCM catalyst precursor aqueous solution with the first calcined supported OCM catalyst precursor, wherein the first calcined supported OCM catalyst precursor comprises a porous support (e.g., alumina-silica), wherein the contacting is performed via incipient wetness impregnation with an aqueous solution comprising one or more compounds comprising an alkaline earth metal (A) cation, one or more compounds comprising a first rare earth element (Z) cation, one or more compounds comprising a second rare earth element (E) cation, and optionally one or more compounds comprising a redox agent or a third rare earth element (D) cation, to form a second impregnated support, in a manner similar to forming the first impregnated support as previously described herein. The second impregnated support can then be dried and calcined to drive off the volatile components within the solution, depositing the one or more compounds comprising an A cation, one or more compounds comprising a Z cation, one or more compounds comprising an E cation, and optionally one or more compounds comprising a D cation on the first single oxide layer outer external surface.

In an aspect, the step of forming the second OCM catalyst precursor mixture can comprise drying at least a portion of the second OCM catalyst precursor mixture at a temperature of equal to or greater than about 75° C., about 90° C., about 100° C., about 110° C., or about 125° C., alternatively from about 75° C. to about 400° C., about 80° C. to about 400° C., about 100° C. to about 400° C., about 125° C. to about 400° C., about 75° C. to about 200° C., about 80° C. to about 200° C., about 100° C. to about 200° C., or about 125° C. to about 200° C., to yield a dried second impregnated support. The second OCM catalyst precursor mixture can be dried for a time period of equal to or greater than about 2 h, about 4 h, about 8 h, or about 12 h, to yield the dried second impregnated support.

In an aspect, a method of making a multilayer supported OCM catalyst composition as disclosed herein can comprise a step of calcining at least a portion of the second supported OCM catalyst precursor (e.g., second impregnated support, dried second impregnated support) to form a second calcined supported OCM catalyst precursor, wherein the second calcined supported OCM catalyst precursor comprises the support, the first single oxide layer, and the one or more mixed oxide layers; wherein the one or more mixed oxide layers contacts the first single oxide layer outer external surface and optionally the support (in aspects where the first single oxide layer contacts less than about 100% of the external surface of the support); and wherein the one or more mixed oxide layers is characterized by the general formula $A_{a2}Z_{b2}E_{c2}D_{d2}O_{x2}$, wherein a2 is 1.0; wherein b2 is from about 0.1 to about 10.0; wherein c2 is from about 0.1 to about 10.0; wherein d2 is from about 0 to about 10.0; wherein x2 balances the oxidation states.

The second supported OCM catalyst precursor (e.g., second impregnated support, dried second impregnated support) can be calcined at a temperature of equal to or greater than about 500° C., about 550° C., about 600° C., about 650° C., about 700° C., about 750° C., about 800° C., about 850° C., or about 900° C., alternatively from about 500° C. to about 1,100° C., about 550° C. to about 1,100° C., about 600° C. to about 1,100° C., 750° C. to about 1,100° C., about 800° C. to about 1,100° C., about 850° C. to about 1,100° C., or about 900° C. to about 1,100° C., to yield the second calcined supported OCM catalyst precursor. The second supported OCM catalyst precursor (e.g., second impregnated support, dried second impregnated support) can be calcined for a time period of equal to or greater than about 2 h, about 4 h, or about 6 h.

In some aspects, at least a portion of the second supported OCM catalyst precursor (e.g., second impregnated support, dried second impregnated support) can be calcined in an oxidizing atmosphere (e.g., in an atmosphere comprising $O_2$, for example in air) to form the second calcined supported OCM catalyst precursor. Without wishing to be limited by theory, a portion of the oxygen in the second calcined supported OCM catalyst precursor having the one or more mixed oxide layers characterized by the general formula $A_{a2}Z_{b2}E_{c2}D_{d2}O_{x2}$ can originate in the oxidizing atmosphere used for calcining the second supported OCM catalyst precursor. Further, without wishing to be limited by theory, a portion of the oxygen in the second calcined supported OCM catalyst precursor having the one or more mixed oxide layers characterized by the general formula $A_{a2}Z_{b2}E_{c2}D_{d2}O_{x2}$ can originate in the one or more compounds comprising an alkaline earth metal cation, one or more compounds comprising a first rare earth element cation, one or more compounds comprising a second rare earth element cation, and one or more compounds comprising a redox agent cation or a third rare earth element cation used for forming the one or more mixed oxide layers, provided that at least one of these compounds comprises oxygen in its formula (e.g., nitrates, oxides, hydroxides, acetates, carbonates, etc.).

In some aspects, the second calcined supported OCM catalyst precursor can be employed as the multilayer supported OCM catalyst composition as disclosed herein, for example in an OCM reaction.

In other aspects, the second calcined supported OCM catalyst precursor can be further subjected to one or more additional steps of depositing one or more additional mixed oxide layers as disclosed herein, as necessary to achieve a target thickness for the one or more mixed oxide layers. For example, at least a portion of the second calcined supported OCM catalyst precursor can be contacted as disclosed herein with an OCM catalyst precursor mixture (e.g., second OCM catalyst precursor mixture), followed by drying as disclosed herein at a temperature of equal to or greater than about 75° C. for a time period of equal to or greater than about 2 h, and by calcining as disclosed herein at a temperature of equal to or greater than about 500° C. for a time period of equal to or greater than about 2 h. The OCM catalyst precursor mixture (e.g., second OCM catalyst precursor mixture) can comprise one or more compounds comprising an alkaline earth metal (A) cation, one or more compounds comprising a first rare earth element (Z) cation, one or more compounds comprising a second rare earth element (E) cation, and one or more compounds comprising a redox agent cation or a third rare earth element (D) cation; wherein the first rare earth element cation, the second rare earth element cation, and the third rare earth element cation, when present, are not the same (i.e., are different). The second calcined supported OCM catalyst precursor can be impregnated (e.g., via incipient wetness impregnation) with an OCM catalyst precursor mixture (e.g., second OCM catalyst precursor mixture) as disclosed herein. Impregnating the second calcined supported OCM catalyst precursor with an OCM catalyst precursor mixture (e.g., second OCM catalyst precursor mixture), followed by drying and calcining as disclosed herein can be repeated as necessary to achieve a target thickness for the one or more mixed oxide layers.

As will be appreciated by one of skill in the art, and with the help of this disclosure, each additional step of depositing an additional mixed oxide layer as disclosed herein may deposit an additional mixed oxide layer that can be characterized by substantially the same composition as the overall one or mixed oxide layers (i.e., a composition characterized by the general formula $A_{a2}Z_{b2}E_{c2}D_{d2}O_{x2}$), and/or by substantially the same composition of at least one adjacent mixed oxide layer; or alternatively, the additional mixed oxide layer can be characterized by a composition that is different from the overall composition of the one or mixed oxide layers, and/or different from the composition of at least one adjacent mixed oxide layer.

In an aspect, a method of making a multilayer supported OCM catalyst composition as disclosed herein can further comprise subjecting at least a portion of the second calcined supported OCM catalyst precursor to one or more steps of depositing a second single oxide layer onto the second calcined supported OCM catalyst precursor to form the multilayer supported OCM catalyst composition, wherein the multilayer supported OCM catalyst composition comprises the support, the first single oxide layer, the one or more mixed oxide layers, and the second single oxide layer; wherein the second single oxide layer contacts the one or more mixed oxide layers, and optionally the first single oxide layer outer external surface and/or the external surface of the support; and wherein the second single oxide layer is characterized by the general formula AO.

In an aspect, at least a portion of the second calcined supported OCM catalyst precursor can be contacted with a third OCM catalyst precursor mixture to form a third supported OCM catalyst precursor, wherein the third OCM catalyst precursor mixture comprises one or more compounds comprising an alkaline earth metal cation (A). For purposes of the disclosure herein, all descriptions related to steps of depositing the first single oxide layer onto the support (such as descriptions of a step of forming or otherwise obtaining an OCM catalyst precursor mixture (e.g., first OCM catalyst precursor mixture); a step of contacting at least a portion of an OCM catalyst precursor mixture (e.g., first OCM catalyst precursor mixture) with a support, such as impregnation (e.g., incipient wetness impregnation); a step of drying the first OCM catalyst precursor mixture; a step of calcining the first supported OCM catalyst precursor; etc.) can be applied to the corresponding steps of depositing the second single oxide layer onto the second calcined supported OCM catalyst precursor (such as descriptions of a step of forming or otherwise obtaining an OCM catalyst precursor mixture (e.g., third OCM catalyst precursor mixture); a step of contacting at least a portion of an OCM catalyst precursor mixture (e.g., third OCM catalyst precursor mixture) with a second calcined supported OCM catalyst precursor, such as impregnation (e.g., incipient wetness impregnation); a step of drying the third OCM catalyst precursor mixture; a step of calcining the third supported OCM catalyst precursor; etc.; respectively), unless otherwise specified herein.

In an aspect, subjecting the second calcined supported OCM catalyst precursor to depositing a second single oxide layer can comprise (1) solubilizing the one or more compounds comprising an alkaline earth metal cation in an aqueous medium to form the third OCM catalyst precursor mixture, wherein the third OCM catalyst precursor mixture comprises the one or more compounds comprising an alkaline earth metal cation and the aqueous medium; (2) contacting at least a portion of the second calcined supported OCM catalyst precursor with at least a portion of the third OCM catalyst precursor mixture to form the third supported OCM catalyst precursor; (3) optionally drying at least a portion of the third supported OCM catalyst precursor at a temperature of equal to or greater than about 75° C. for a time period of equal to or greater than about 2 h; and (4) calcining at least a portion of the third supported OCM catalyst precursor (optionally dried) at a temperature of equal to or greater than about 500° C. for a time period of equal to or greater than about 2 h to yield a third calcined supported OCM catalyst precursor, wherein the third calcined supported OCM catalyst precursor comprises the support, the first single oxide layer, the one or more mixed oxide layers, and the second single oxide layer; wherein the second single oxide layer contacts the one or more mixed oxide layers outer external surface, and optionally the first single oxide layer outer external surface and/or the external surface of the support; and wherein the second single oxide layer is characterized by the general formula AO.

In some aspects, the third calcined supported OCM catalyst precursor can be employed as the multilayer supported OCM catalyst composition as disclosed herein, for example in an OCM reaction.

In other aspects, the third calcined supported OCM catalyst precursor can be further subjected to one or more additional steps of depositing an additional second single oxide layer as disclosed herein, as necessary to achieve a target amount of the second single oxide layer in the multilayer supported OCM catalyst composition. For example, the target amount of the second single oxide layer in the multilayer supported OCM catalyst composition can be from about 0.1 wt. % to about 20.0 wt. %, based on the total weight of the metal oxide component.

In an aspect, at least a portion of the third calcined supported OCM catalyst precursor can be contacted with an OCM catalyst precursor mixture (e.g., third OCM catalyst precursor mixture), followed by drying as disclosed herein at a temperature of equal to or greater than about 75° C. for a time period of equal to or greater than about 2 h, and by calcining as disclosed herein at a temperature of equal to or greater than about 500° C. for a time period of equal to or greater than about 2 h. The OCM catalyst precursor mixture (e.g., third OCM catalyst precursor mixture) can comprise one or more compounds comprising an alkaline earth metal (A) cation. The third calcined supported OCM catalyst precursor can be impregnated (e.g., via incipient wetness impregnation) with an OCM catalyst precursor mixture (e.g., third OCM catalyst precursor mixture) as disclosed herein. Impregnating the third calcined supported OCM catalyst precursor with an OCM catalyst precursor mixture (e.g., third OCM catalyst precursor mixture), followed by drying and calcining as disclosed herein can be repeated as necessary to achieve a target amount of the second single oxide layer in the multilayer supported OCM catalyst composition.

As will be appreciated by one of skill in the art, and with the help of this disclosure, and without wishing to be limited by theory, given the relatively low amount of second single oxide layer in the multilayer supported OCM catalyst composition (e.g., from about 0.1 wt. % to about 20.0 wt. %, based on the total weight of the metal oxide component), as well as the relatively low surface area coverage (e.g., the second single oxide layer may contact from about 5% to about 50% of the outer external surface of the one or more mixed oxide layers), it is likely that additional second single oxide layer material (i.e., AO) would be deposited on available (i.e., uncovered, not covered by second single oxide layer material) outer external surface of the one or more mixed oxide layers; as opposed to being deposited onto existing second single oxide layer material. Consequently, additional second single oxide layer material is likely to increase the surface area coverage (e.g., the amount for the second single oxide layer in the multilayer supported OCM catalyst composition), as opposed to increasing the thickness of the second single oxide layer.

As will be appreciated by one of skill in the art, and with the help of this disclosure, each additional step of depositing additional second single oxide layer material may deposit an additional alkaline earth metal oxide material that can be characterized by substantially the same composition as the overall second single oxide layer (i.e., a composition characterized by the general formula AO), and/or by substantially the same composition of at least a portion of the overall second single oxide layer; or alternatively, the additional alkaline earth metal oxide material can be characterized by a composition that is different from the overall second single oxide layer (i.e., a composition characterized by the general formula AO), and/or different from the composition of at least a portion of the overall second single oxide layer.

In an aspect, a method of making a multilayer supported OCM catalyst composition as disclosed herein can further comprise a step of sizing the multilayer supported OCM catalyst composition to form the multilayer supported OCM catalyst composition into desired particle specifications (e.g., required particle specifications). The multilayer supported OCM catalyst composition can be sized by using any suitable methodology. In an aspect, the multilayer supported OCM catalyst composition can be subjected to grinding, crushing, milling, chopping, and the like, or combinations thereof to form the multilayer supported OCM catalyst composition into desired particle specifications (e.g., required particle specifications). As previously described herein, the multilayer supported OCM catalyst composition can have any suitable desired particle specifications, for example as required by a specific application.

As will be appreciated by one of skill in the art, and with the help of this disclosure, sizing the multilayer supported OCM catalyst composition into desired particle specifications (e.g., required particle specifications) could provide for exposing a cross-section of the metal oxide component (i.e., $A_aZ_bE_cD_dO_x$), as well as a cross-section of the support component (i.e., support), for example to reactants (e.g., $CH_4$, $O_2$) in an OCM reaction. Consequently, a cross-section of the first single oxide layer, a cross-section of the one or more mixed oxide layers, a cross-section of the second single oxide layer, etc. could be exposed to reactants (e.g., $CH_4$, $O_2$) in an OCM reaction, in addition to an external surface of the first single oxide layer, an external surface of the one or more mixed oxide layers, an external surface of the second single oxide layer, etc. being exposed to reactants (e.g., $CH_4$, $O_2$) in an OCM reaction.

A method for producing olefins as disclosed herein can comprise (A) introducing a reactant mixture (e.g., OCM reactant mixture) comprising $CH_4$ and $O_2$ to an OCM reactor comprising the multilayer supported OCM catalyst composition as disclosed herein; and (B) allowing at least a portion of the reactant mixture to contact at least a portion of the multilayer supported OCM catalyst composition and react via an OCM reaction to form a product mixture comprising unreacted methane and olefins.

The OCM reactant mixture can be a gaseous mixture. The OCM reactant mixture can comprise a hydrocarbon or mixtures of hydrocarbons, and $O_2$. In some aspects, the hydrocarbon or mixtures of hydrocarbons can comprise natural gas (e.g., $CH_4$), liquefied petroleum gas comprising $C_2$-$C_5$ hydrocarbons, $C_{6+}$ heavy hydrocarbons (e.g., $C_6$ to $C_{24}$ hydrocarbons such as diesel fuel, jet fuel, gasoline, tars, kerosene, etc.), oxygenated hydrocarbons, biodiesel, alcohols, dimethyl ether, and the like, or combinations thereof. In an aspect, the OCM reactant mixture can comprise $CH_4$ and $O_2$. The $O_2$ used in the OCM reactant mixture can be $O_2$ gas (which may be obtained via a membrane separation process), technical $O_2$ (which may contain some air), air, $O_2$ enriched air, and the like, or combinations thereof.

The OCM reactant mixture can further comprise a diluent. The diluent is inert with respect to the OCM reaction, e.g., does not participate in the OCM reaction. In an aspect, the diluent can comprise water (e.g., steam), nitrogen, inert gases, and the like, or combinations thereof. In an aspect, the diluent can be present in the OCM reactant mixture in an amount of from about 0.5% to about 80%, about 5% to about 50%, or about 10% to about 30%, based on the total volume of the OCM reactant mixture.

The OCM reactor can comprise an adiabatic reactor, an autothermal reactor, an isothermal reactor, a tubular reactor, a cooled tubular reactor, a continuous flow reactor, a fixed bed reactor, a fluidized bed reactor, a moving bed reactor, and the like, or combinations thereof. In an aspect, the OCM reactor can comprise a catalyst bed comprising the multilayer supported OCM catalyst composition.

In an aspect, the OCM reactor can be characterized by any suitable OCM reactor operational parameters, such as temperature (e.g., feed preheat temperature, reactor effluent temperature, etc.), pressure, flow rate (e.g., space velocity), and the like, or combinations thereof.

The OCM reaction mixture can be introduced to the OCM reactor at a temperature (e.g., feed preheat temperature) of from about 150° C. to about 1,000° C., about 225° C. to about 900° C., or about 250° C. to about 800° C. As will be appreciated by one of skill in the art, and with the help of this disclosure, while the OCM reaction is exothermic, heat input is necessary for promoting the formation of methyl radicals from $CH_4$, as the C—H bonds of $CH_4$ are very stable, and the formation of methyl radicals from $CH_4$ is endothermic. In an aspect, the OCM reaction mixture can be introduced to the OCM reactor at a temperature effective to promote an OCM reaction.

The OCM reactor can be characterized by a reactor effluent temperature of from about 400° C. to about 1,200° C., about 500° C. to about 1,100° C., or about 600° C. to about 1,000° C. The OCM reactor can be characterized by a pressure of from about ambient pressure (e.g., atmospheric pressure) to about 500 psig, alternatively about ambient pressure to about 200 psig, or alternatively about ambient pressure to about 150 psig. In an aspect, the method for producing olefins can be carried out at about ambient pressure.

The OCM reactor can be characterized by a gas hourly space velocity (GHSV) of from about 500 h$^{-1}$ to about 10,000,000 h$^{-1}$, about 500 h$^{-1}$ to about 1,000,000 h$^{-1}$, about 500 h$^{-1}$ to about 100,000 h$^{-1}$, about 500 h$^{-1}$ to about 50,000 h$^{-1}$, about 1,000 h$^{-1}$ to about 40,000 h$^{-1}$, or about 1,500 h$^{-1}$ to about 25,000 h$^{-1}$. Generally, the GHSV relates a reactant (e.g., reactant mixture) gas flow rate to a reactor volume. GHSV is usually measured at standard temperature and pressure.

In an aspect, the method for producing olefins as disclosed herein can comprise recovering at least a portion of the product mixture from the OCM reactor, wherein the product mixture can comprise olefins, water, CO, CO$_2$, and unreacted methane. In an aspect, a method for producing olefins as disclosed herein can comprise recovering at least a portion of the olefins from the product mixture. The product mixture can comprise C$_{2+}$ hydrocarbons (including olefins), unreacted methane, and optionally a diluent. The C$_{2+}$ hydrocarbons can comprise C$_2$ hydrocarbons and C$_3$ hydrocarbons. In an aspect, the C$_{2+}$ hydrocarbons can further comprise C$_4$ hydrocarbons (C$_4$s), such as for example butane, iso-butane, n-butane, butylene, etc. The C$_2$ hydrocarbons can comprise C$_2$H$_4$ and C$_2$H$_6$. The C$_2$ hydrocarbons can further comprise acetylene (C$_2$H$_2$). The C$_3$ hydrocarbons can comprise propylene (C$_3$H$_6$) and propane (C$_3$H$_8$).

The water produced from the OCM reaction and the water used as a diluent (if water diluent is used) can be separated from the product mixture prior to separating any of the other product mixture components. For example, by cooling down the product mixture to a temperature where the water condenses (e.g., below 100° C. at ambient pressure), the water can be removed from the product mixture, by using a flash chamber for example.

A method for producing olefins as disclosed herein can comprise recovering at least a portion of the olefins from the product mixture. In an aspect, at least a portion of the olefins can be separated from the product mixture by distillation (e.g., cryogenic distillation). As will be appreciated by one of skill in the art, and with the help of this disclosure, the olefins are generally individually separated from their paraffin counterparts by distillation (e.g., cryogenic distillation). For example, ethylene can be separated from ethane by distillation (e.g., cryogenic distillation). As another example, propylene can be separated from propane by distillation (e.g., cryogenic distillation).

In an aspect, at least a portion of the unreacted methane can be separated from the product mixture to yield recovered methane. Methane can be separated from the product mixture by using any suitable separation technique, such as for example distillation (e.g., cryogenic distillation). At least a portion of the recovered methane can be recycled to the reactant mixture.

In an aspect, the O$_2$ conversion of the OCM reaction as disclosed herein can be equal to or greater than about 90%, about 95%, about 99%, about 99.9%, or alternatively about 100%. Generally, a conversion of a reagent or reactant refers to the percentage (usually mol %) of reagent that reacted to both undesired and desired products, based on the total amount (e.g., moles) of reagent present before any reaction took place. For purposes of the disclosure herein, the conversion of a reagent is a % conversion based on moles converted. As will be appreciated by one of skill in the art, and with the help of this disclosure, the reactant mixture in OCM reactions is generally characterized by a methane to oxygen molar ratio of greater than 1:1, and as such the O$_2$ conversion is fairly high in OCM processes, most often approaching 90%-100%. Without wishing to be limited by theory, oxygen is usually a limiting reagent in OCM processes. The O$_2$ conversion can be calculated by using equation (9):

$$O_2 \text{ conversion} = \frac{O_2^{in} - O_2^{out}}{O_2^{in}} \times 100\% \tag{9}$$

wherein $O_2^{in}$=number of moles of O$_2$ that entered the OCM reactor as part of the reactant mixture; and $O_2^{out}$=number of moles of O$_2$ that was recovered from the OCM reactor as part of the product mixture.

The multilayer supported OCM catalyst composition as disclosed herein can be characterized by a C$_{2+}$ selectivity that is increased when compared to a C$_{2+}$ selectivity of an otherwise similar supported OCM catalyst composition without a multilayer structure. In an aspect, the multilayer supported OCM catalyst composition as disclosed herein can be characterized by a C$_{2+}$ selectivity that is increased by equal to or greater than about 1%, about 2.5%, about 5%, about 7.5%, or about 10% when compared to a C$_{2+}$ selectivity of an otherwise similar supported OCM catalyst composition without a multilayer structure.

Generally, a selectivity to a desired product or products refers to how much desired product was formed divided by the total products formed, both desired and undesired. For purposes of the disclosure herein, the selectivity to a desired product is a % selectivity based on moles converted into the desired product. Further, for purposes of the disclosure herein, a C$_x$ selectivity (e.g., C$_2$ selectivity, C$_{2+}$ selectivity, etc.) can be calculated by dividing a number of moles of carbon (C) from CH$_4$ that were converted into the desired product (e.g., $C_{C2H4}$, $C_{C2H6}$, etc.) by the total number of moles of C from CH$_4$ that were converted (e.g., $C_{C2H4}$, $C_{C2H6}$, $C_{C2H2}$, $C_{C3H6}$, $C_{C3H8}$, $C_{C4s}$, $C_{CO2}$, $C_{CO}$, etc.). $C_{C2H4}$=number of moles of C from CH$_4$ that were converted into C$_2$H$_4$; $C_{C2H6}$=number of moles of C from CH$_4$ that were converted into C$_2$H$_6$; $C_{C2H2}$=number of moles of C from CH$_4$ that were converted into C$_2$H$_2$; $C_{C3H6}$=number of moles of C from CH$_4$ that were converted into C$_3$H$_6$; $C_{C3H8}$=number of moles of C from CH$_4$ that were converted into C$_3$H$_8$; $C_{C4s}$=number of moles of C from CH$_4$ that were converted into C$_4$ hydrocarbons (C$_4$s); $C_{CO2}$=number of moles of C from CH$_4$ that were converted into CO$_2$; etc.

A C$_{2+}$ selectivity (e.g., selectivity to C$_{2+}$ hydrocarbons) refers to how much C$_2$H$_4$, C$_3$H$_6$, C$_2$H$_2$, C$_2$H$_6$, C$_3$H$_8$, and C$_4$s were formed divided by the total products formed, including C$_2$H$_4$, C$_3$H$_6$, C$_2$H$_2$, C$_2$H$_6$, C$_3$H$_8$, C$_4$s, CO$_2$ and CO. For example, the C$_{2+}$ selectivity can be calculated by using equation (10):

$$C_{2+} \text{ selectivity} = \frac{2C_{C_2H_4} + 2C_{C_2H_6} + 2C_{C_2H_2} + 3C_{C_3H_6} + 3C_{C_3H_8} + 4C_{C_{4s}}}{2C_{C_2H_4} + 2C_{C_2H_6} + 2C_{C_2H_2} + 3C_{C_3H_6} + 3C_{C_3H_8} + 4C_{C_{4s}} + C_{CO_2} + C_{CO}} \times 100\% \tag{10}$$

As will be appreciated by one of skill in the art, and with the help of this disclosure, if a specific product and/or hydrocarbon product is not produced in a certain OCM reaction/process, then the corresponding $C_{Cx}$ is 0, and the term is simply removed from selectivity calculations.

In an aspect, the multilayer supported OCM catalyst composition as disclosed herein can be characterized by the general formula Sr$_a$La$_b$Yb$_c$Nd$_d$O$_x$/support, wherein the multilayer supported OCM catalyst composition comprises a support, a first single oxide layer, one or more mixed oxide layers, and an optional second single oxide layer; wherein a is 1.0; b is from about 0.1 to about 10.0; c is from about 0.1 to about 10.0; d is from about 0 to about 10.0; and x balances the oxidation states; wherein the first single oxide layer contacts the support and the one or more mixed oxide layers, wherein the first single oxide layer comprises $La_2O_3$; wherein the one or more mixed oxide layers contacts the first single oxide layer and the second single oxide layer, wherein the one or more mixed oxide layers is characterized by the general formula $Sr_{a2}La_{b2}Yb_{c2}Nd_{d2}O_{x2}$, wherein a2 is 1.0; b2 is from about 0.1 to about 10.0; c2 is from about 0.1 to about 10.0; d2 is from about 0 to about 10.0; and x2 balances the oxidation states; wherein the general formula $Sr_aLa_bYb_cNd_dO_x$ and the general formula $Sr_{a2}La_{b2}Yb_{c2}Nd_{d2}O_{x2}$ are different; wherein the second single oxide layer contacts the one or more mixed oxide layers and optionally the first single oxide layer, and wherein the second single oxide layer comprises SrO.

In an aspect, a method of making a multilayer supported OCM catalyst composition as disclosed herein can comprise the steps of (a) solubilizing one or more compounds comprising a first rare earth element cation in an aqueous medium to form a first OCM catalyst precursor mixture; (b) contacting a support with at least a portion of the first OCM catalyst precursor mixture to form a first supported OCM catalyst precursor comprising the one or more compounds comprising a first rare earth element cation and the aqueous medium; (c) drying at least a portion of the first OCM catalyst precursor at a temperature of equal to or greater than about 75° C. to form a dried first supported OCM catalyst precursor; (d) calcining at least a portion of the dried first supported OCM catalyst precursor at a temperature of equal to or greater than about 500° C. to form a first calcined supported OCM catalyst precursor comprising the support and a first single oxide layer, wherein the first single oxide layer contacts the support, wherein the first single oxide layer is characterized by the general formula $Z_{b1}O_{x1}$, wherein b1 is from about 0.1 to about 10.0; and wherein x1 balances the oxidation states; (e) solubilizing one or more compounds comprising an alkaline earth metal cation, one or more compounds comprising a first rare earth element cation, one or more compounds comprising a second rare earth element cation, and one or more compounds comprising a redox agent cation or a third rare earth element cation in an aqueous medium to form a second OCM catalyst precursor mixture; (f) contacting at least a portion of the first calcined supported OCM catalyst precursor with at least a portion of the second OCM catalyst precursor mixture to form a second supported OCM catalyst precursor comprising one or more compounds comprising an alkaline earth metal (A) cation, one or more compounds comprising a first rare earth element (Z) cation, one or more compounds comprising a second rare earth element (E) cation, and one or more compounds comprising a redox agent cation or a third rare earth element (D) cation; wherein the first rare earth element cation, the second rare earth element cation, and the third rare earth element cation, when present, are not the same; wherein the second OCM catalyst precursor mixture is characterized by a molar ratio of first rare earth element to alkaline earth metal of b2:1, wherein b2 is from about 0.1 to about 10.0; wherein the second OCM catalyst precursor mixture is characterized by a molar ratio of second rare earth element to alkaline earth metal of c2:1, wherein c2 is from about 0.1 to about 10.0; and wherein the second OCM catalyst precursor mixture is characterized by a molar ratio of redox agent or third rare earth element to alkaline earth metal of d2:1, wherein d2 is from about 0 to about 10.0; (g) drying at least a portion of the second supported OCM catalyst precursor at a temperature of equal to or greater than about 75° C. to form a dried second supported OCM catalyst precursor; (h) calcining at least a portion of the dried second supported OCM catalyst precursor at a temperature of equal to or greater than about 500° C. to form a second calcined supported OCM catalyst precursor comprising the support, the first single oxide layer, and one or more mixed oxide layers; wherein the one or more mixed oxide layers contacts the first single oxide layer and optionally the support; and wherein the one or more mixed oxide layers is characterized by the general formula $A_{a2}Z_{b2}E_{c2}D_{d2}O_{x2}$, wherein a2 is 1.0; wherein b2 is about 0.1 to about 10.0; wherein c2 is about 0.1 to about 10.0; wherein d2 is about 0 to about 10.0; wherein x2 balances the oxidation states; (i) solubilizing one or more compounds comprising an alkaline earth metal cation in an aqueous medium to form a third OCM catalyst precursor mixture comprising the one or more compounds comprising an alkaline earth metal cation and the aqueous medium; (j) contacting at least a portion of the second calcined supported OCM catalyst precursor with at least a portion of the third OCM catalyst precursor mixture to form a third supported OCM catalyst precursor; (k) drying at least a portion of the third supported OCM catalyst precursor at a temperature of equal to or greater than about 75° C. for a time period of equal to or greater than about 2 h to form a dried third supported OCM catalyst precursor; and (l) calcining at least a portion of the dried third supported OCM catalyst precursor at a temperature of equal to or greater than about 500° C. for a time period of equal to or greater than about 2 h to yield a multilayer supported OCM catalyst composition as disclosed herein; wherein the multilayer supported OCM catalyst composition comprises the support, the first single oxide layer, the one or more mixed oxide layers, and the second single oxide layer; wherein the second single oxide layer contacts the one or more mixed oxide layers, and optionally the first single oxide layer outer external surface and/or the external surface of the support; and wherein the second single oxide layer is characterized by the general formula AO; wherein the multilayer supported OCM catalyst composition is characterized by the general formula $A_aZ_bE_cD_dO_x$/support, wherein a is 1.0; wherein b is about 0.1 to about 10.0; wherein c is about 0.1 to about 10.0; wherein d is about 0 to about 10.0; wherein x balances the oxidation states; and wherein Z, E, and D, when present, are not the same. In such aspect, steps (e)-(h) can be repeated as necessary to achieve a target thickness for the one or more mixed oxide layers; and/or steps (i)-(l) can be repeated as necessary to achieve a target amount of the second single oxide layer in the multilayer supported OCM catalyst composition.

The multilayer supported OCM catalyst composition characterized by the general formula $A_aZ_bE_cD_dO_x$/support; and methods of making and using same, as disclosed herein can advantageously display improvements in one or more composition characteristics when compared to conventional OCM catalysts, e.g., otherwise similar supported OCM catalyst compositions without a multilayer structure. The multilayer supported OCM catalyst composition as disclosed herein can advantageously display improved conversion, $C_{2+}$ selectivity, activity and stability when compared to the conversion, $C_{2+}$ selectivity, activity and stability, respectively, of an otherwise similar supported OCM catalyst composition without a multilayer structure. The multilayer supported OCM catalyst compositions as disclosed herein can advantageously display improved conversion, $C_{2+}$ selectivity, activity and stability owing to the synergetic effects of catalytic material layers forming the multilayer supported OCM catalyst compositions.

In an aspect, the multilayer supported OCM catalyst composition as disclosed herein can be advantageously characterized by a $C_{2=}$ selectivity (selectivity to acetylene) that is decreased when compared to a $C_{2=}$ selectivity of conventional OCM catalysts (e.g., otherwise similar supported OCM catalyst compositions without a multilayer structure). Additional advantages of the multilayer supported OCM catalyst compositions as disclosed herein; and methods of making and using same, can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Example 1

Oxidative coupling of methane (OCM) catalyst compositions were prepared as follows.

Reference catalyst #1 ($Sr_{1.0}La_{1.8}Nd_{0.7}Yb_{0.1}O_x$) was prepared by using the following procedure. 10.58 g of $Sr(NO_3)_2$, 19.48 g of $La(NO_3)_3 \cdot 6H_2O$, 15.35 g of $Nd(NO_3)_3 \cdot 6H_2O$ and 2.26 g of $Yb(NO_3)_3 \cdot 5H_2O$ were mixed and dissolved into 100 ml water. The obtained mixture was dried at 125° C. overnight, and then calcined at 900° C. for 6 hours to produce the reference catalyst #1 ($Sr_{1.0}La_{1.8}Nd_{0.7}Yb_{0.1}O_x$) which is a bulk catalyst, as opposed to a multilayered supported catalyst.

Reference catalyst #2 ($Mn—Na_2WO_4/SiO_2$) was prepared by using the following procedure. Silica gel (18.6 g, Davisil® Grade 646) was used after drying overnight. $Mn(NO_3)_2 \cdot 4H_2O$ (1.73 g) was dissolved in deionized water (18.5 mL), and then added dropwise onto the silica gel. The resulting manganese impregnated silica material was dried overnight. $Na_2WO_4 \cdot 2H_2O$ (1.22 g) was dissolved in deionized water (18.5 mL), and the solution obtained was added onto the dried manganese silica material above. The resulting material obtained was dried overnight at 125° C., and then calcined at 800° C. for 6 h under airflow to obtain the reference catalyst #2 ($Mn—Na_2WO_4/SiO_2$).

Multilayer supported OCM catalyst compositions as disclosed herein were prepared according to the flow diagram displayed in FIG. 1. According to FIG. 1, the method 1000 of making the multilayer supported OCM catalyst compositions as disclosed herein comprised the following steps: a step 100 of drying the support at 200° C. for 12 h; a step 200 of impregnating the support with $La(NO_3)_3 \cdot 6H_2O$, followed by drying and calcination; a step 300 of impregnating the calcined material resulting from step 200 with nitrate solutions ($Sr(NO_3)_2$, $La(NO_3)_3 \cdot 6H_2O$, $Nd(NO_3)_3 \cdot 6H_2O$, $Yb(NO_3)_3 \cdot 5H_2O$), followed by drying and calcination; a step 400 of repeating step 300 if necessary; and an optional step 500 of impregnating the calcined material resulting from steps 300/400 with $Sr(NO_3)_2$, followed by drying and calcination to produce the multilayer supported OCM catalyst compositions. Different multilayer supported OCM catalyst compositions containing Sr, La, Yb, and Nd (e.g., catalysts #1, #2, #3, #4, #5, and #6) were prepared according to the flow diagram displayed in FIG. 1, by using the corresponding amounts of $Sr(NO_3)_2$, $La(NO_3)_3 \cdot 6H_2O$, $Nd(NO_3)_3 \cdot 6H_2O$, $Yb(NO_3)_3 \cdot 5H_2O$, as necessary to obtain a catalyst with the desired general formula.

Example 2

The performance of the multilayer supported OCM catalyst compositions prepared as described in Example 1 was investigated and compared to the performance of the reference catalysts. OCM reactions were conducted by using catalysts prepared as described in Example 1 as follows.

Performance test. The catalysts obtained as described in Example 1 were performance tested in a 2.3 mm ID quartz tube reactor. The catalysts were sized to 35-60 mesh prior to loading into the OCM reactor. The reactor was loaded with 20 mg of catalyst. A mixture of methane and $O_2$ at a fixed $CH_4:O_2$ ratio of 7.4 was fed to the reactor at a total flow rate of 40.0 sccm. Products obtained were analyzed by using online GC with TCD and FID detectors.

Figure 2:
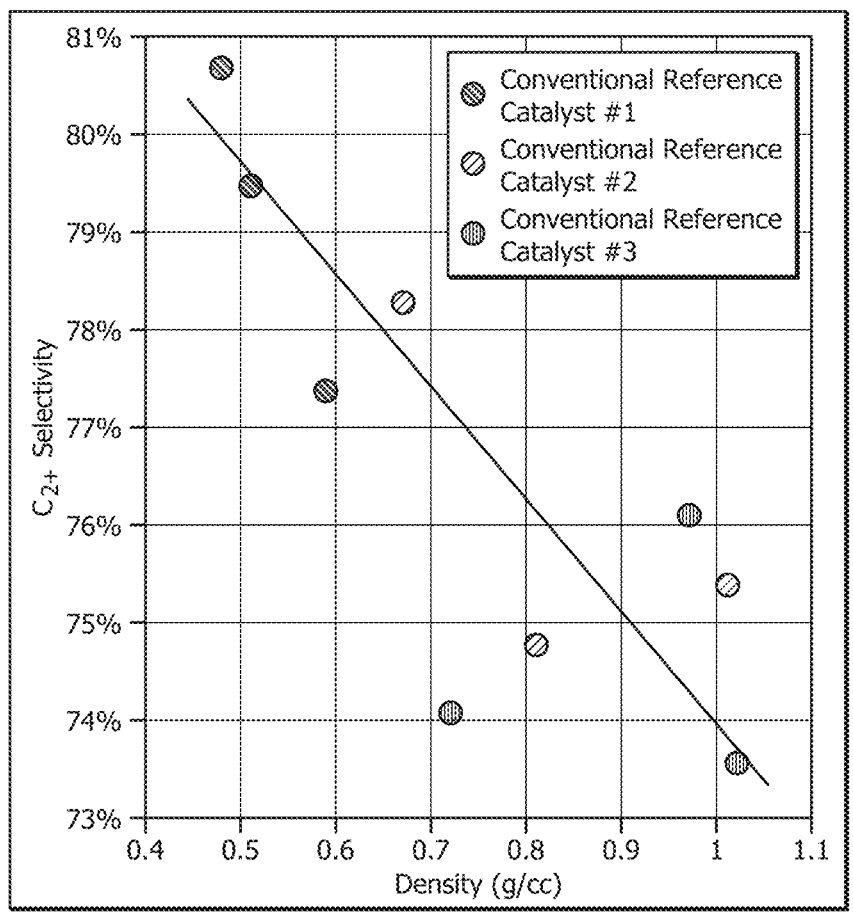
FIG. 2 displays a graph of $C_{2+}$ selectivity as a function of density for various particle catalyst densities of a reference catalyst.

For the reference catalyst #1 ($Sr_{1.0}La_{1.8}Nd_{0.7}Yb_{0.1}O_x$), which is a unsupported bulk catalyst, its performance was high, with about 80% $C_{2+}$ selectivity obtained, when its density was low, at about 0.5 g/cc. However, the strength of the low density catalyst is low and thus it is not suitable for larger reactor loading. Increasing the catalyst strength with compression would result in its density is also increasing. Selectivities obtained with conventional reference catalysts with different densities is displayed in FIG. 2, where it can be seen that with increasing the catalyst density, the selectivity is reduced significantly. Therefore, poorer performance would be obtained when the reference catalyst #1 would be compressed to the required strength for large reactor applications. The multilayer supported OCM catalyst compositions rely on the mechanical strength of the support, such that no compression altering the density of the catalyst is employed.

The performances of multilayer supported OCM catalyst compositions as disclosed herein for catalysts #1, #2, and #3 are shown in Table 1.

TABLE 1

Multilayer Supported OCM Catalyst Compositions with Different layers of Catalytic Components

| Catalyst | Layers loaded | $C_{2+}$ selectivity (%) |
| --- | --- | --- |
| Catalyst #1 | $La_2O_3$ + 1× $Sr_{1.0}La_{1.8}Nd_{0.7}Yb_{0.1}Ox$ loading | 77.0 |
| Catalyst #2 | $La_2O_3$ + 3× $Sr_{1.0}La_{1.8}Nd_{0.7}Yb_{0.1}Ox$ loading | 78.0 |
| Catalyst #3 | $La_2O_3$ + 3× $Sr_{1.0}La_{1.8}Nd_{0.7}Yb_{0.1}Ox$ loading + 1× SrO loading | 79.0 |

Catalyst #1 was prepared with the loading of $La_2O_3$ and with loading 1 layer of $Sr_{1.0}La_{1.8}Nd_{0.7}Yb_{0.1}O_x$, wherein 77.0% $C_{2+}$ selectivity was obtained with catalyst #1. Catalyst #2 was prepared with 2 additional layers of $Sr_{1.0}La_{1.8}Nd_{0.2}Yb_{0.1}O_x$ loaded on the top of a catalyst similar to catalyst #1, wherein 78.0% $C_{2+}$ selectivity was obtained with catalyst #2. Catalyst #3 was prepared with further loading of 1 layer of SrO on the top of a catalyst similar to catalyst #2, and it can be seen that the selectivity was increased to 79.0% for catalyst #3. It can be seen from the data in Table 1 that the multilayer supported OCM catalyst compositions as disclosed herein demonstrated high performance.

Figure 3:
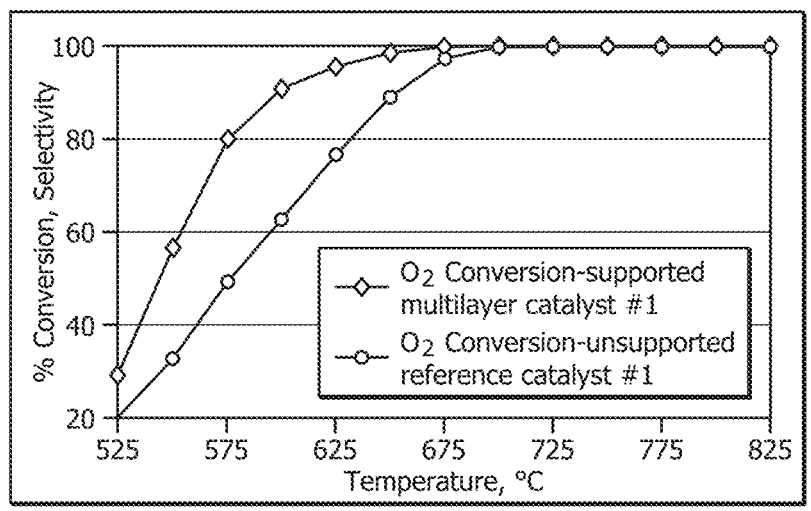
FIG. 3 displays a graph of oxygen ($O_2$) conversion as a function of temperature in an OCM reaction for two different catalysts.

FIG. 3 compares the $O_2$ conversion of catalyst #1 with the $O_2$ conversion of the reference catalyst #1. It can be seen from FIG. 3 that the multilayer catalyst #1 can achieve higher $O_2$ conversion at the same reactor temperature, indicating a higher catalyst activity for catalyst #1. Since there is only 36 wt. % catalyst loading when catalyst #1 is used (64 wt. % is the support), and since the performance testing is carried out with the same total weight of catalyst, the activity data in FIG. 3 further indicate that significantly higher activity is demonstrated with catalyst #1 than with the bulk reference catalyst #1.

Figure 4:
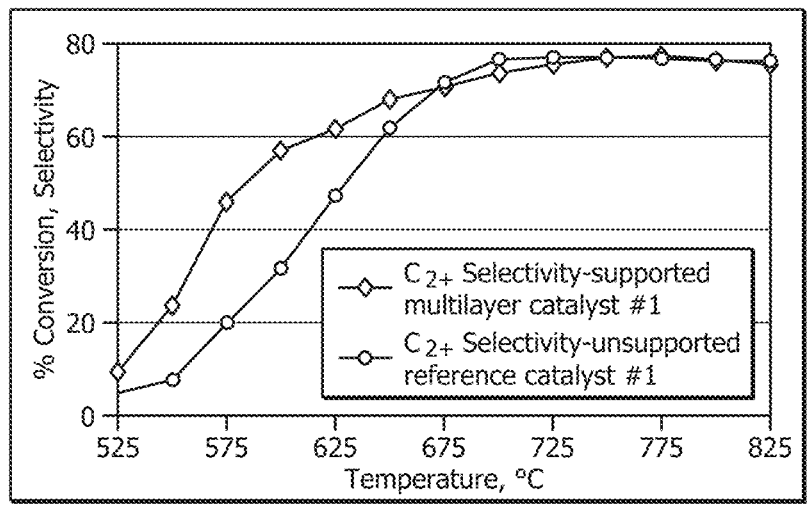
FIG. 4 displays a graph of $C_{2+}$ selectivity as a function of temperature in an OCM reaction for two different catalysts.

FIG. 4 compares the $C_{2+}$ selectivity of the multilayer catalyst #1 with the $C_{2+}$ selectivity of the bulk reference catalyst #1. It can be seen that the multilayer catalyst #1 can achieve the same selectivity as the reference catalyst #1 (which is a low density bulk catalyst). Since the support provides the required strength for the multilayer catalyst #1, no extra compression is needed for the multilayer catalyst #1 to be used in a larger reactor; which is different from the bulk reference catalyst #1 which would require compression resulting in a significant decrease in $C_{2+}$ selectivity in order to be employed in a larger reactor. Therefore, in the context of a larger reactor for commercial/industrial applications, the selectivity obtained with the multilayer catalyst #1 should be compared against the selectivity of the bulk reference catalyst #1 after compression. When comparing the $C_{2+}$ selectivity of the multilayer catalyst #1 with the $C_{2+}$ selectivity of the bulk reference catalyst #1 compressed to a density of 1.0 g/cc, 5%+higher selectivity is obtained with the catalyst #1, clearly demonstrating the advantage of the multilayer catalyst.

Overall, the multilayer supported OCM catalyst compositions as disclosed herein demonstrated higher activity and higher selectivity than the bulk reference catalyst, wherein the multilayer supported OCM catalyst compositions have the required mechanical strength for commercial reactors.

Example 3

The performance of the multilayer supported OCM catalyst compositions prepared as described in Example 1 was investigated and compared to the performance of the reference catalysts as described in Example 2. More specifically, the influence of the amount of SrO loaded onto the catalyst was investigated. The performance of catalysts #3, #4, and #5 is shown in Table 2.

TABLE 2

Multilayer Supported OCM Catalyst Compositions with Different SrO Loadings

| Catalyst | SrO loaded in the last layer | Temperature required to reach 90% $O_2$ conversion, ° C. | $C_{2+}$ selectivity (%) |
|---|---|---|---|
| Catalyst #3 | Base (1×) | 625 | 79.0 |
| Catalyst #4 | Double (2×) | 750 | 80.7 |
| Catalyst #5 | Triple (3×) | 800 | 81.5 |

Catalysts #3, #4, and #5 were made with the same layers of components, but with different last layer SrO content. It can be seen that with higher SrO content, higher $C_{2+}$ selectivity was obtained. At the same time, however, the catalyst activity was decreased with increasing the SrO content, which is indicated by an increase in the temperature needed to reach 90% $O_2$ conversion. As will be appreciated by one of skill in the art, and with the help of this disclosure, the higher the temperature needed to reach 90% $O_2$ conversion, the lower the activity of the catalyst is. Further, the selectivity obtained with catalyst #5 cannot be achieved with a bulk catalyst with about the same composition (e.g., bulk reference catalyst #1, which demonstrates that there is a synergetic effect between the layers of the metal oxide component and the support component of the multilayer supported OCM catalyst composition.

The performance of catalysts #3, and #6 is shown in in Table 3.

TABLE 3

Multilayer Supported OCM Catalyst Compositions Calcined at Different Temperatures

| Catalyst | Calcination Temperature (C.) | Temperature required to reach 90% $O_2$ conversion, ° C. | $C_{2+}$ selectivity (%) |
|---|---|---|---|
| Catalyst #3 | 900 | 625 | 79.0 |
| Catalyst #6 | 650 | 600 | 77.5 |

Catalysts #3, and #6 were made with the same layers of components and with the same amount catalyst components, but were treated at with different calcination temperatures after the last layer (SrO) loading. It can be seen that higher $C_{2+}$ selectivity was obtained with the higher calcination temperature. At the same time, the catalyst activity was decreased slightly with increasing the calcination temperature, which is indicated by a 25° C. increase in the temperature needed to reach 90% $O_2$ conversion.

Example 4

The performance of the multilayer supported OCM catalyst compositions prepared as described in Ex. 1 was investigated and compared to the performance of the reference catalysts as described in Ex. 2. Specifically, the performance of multilayer supported OCM catalyst compositions was compared to the performance of the reference catalyst #2 as displayed in Table 4.

TABLE 4

Performance comparisons of Catalyst #3 and Reference Catalyst #2 (Mn-Na$_2$WO$_4$/SiO$_2$)

| Catalyst | WHSV (hr$^{-1}$) | C$_{2+}$ selectivity (%) | C$_{2+}$ – C$_{2=}$ selectivity (useful selectivity, %) | Deactivation Rate (hr$^{-1}$) |
|---|---|---|---|---|
| Reference Catalyst #2 | 20,000 | 82.0 | 81.0 | 0.066 |
| Catalyst #3 | 240,000 | 81.5 | 81.5 | 0.0012 |

Conventional reference catalyst #2 (Mn—Na$_2$WO$_4$/SiO$_2$) is well known for its high selectivity. However, in the C$_{2+}$ products obtained with the conventional reference catalyst #2, there is about 1% acetylene. Further, acetylene is not desirable for certain ethylene applications, for example, for the production of polyethylene. The multilayer catalyst #3 produces substantially no acetylene in the products, and therefore, the useful C$_{2+}$ selectivity of the multilayer catalyst #3 is higher than the useful C$_{2+}$ selectivity of the conventional reference catalyst #2.

The stability of the multilayer catalyst #3 and the stability of the conventional reference catalyst #2 were tested for more than 60 hours to compare their performance. The results obtained are also shown in Table 4. It can be seen that the multilayer catalyst #3 is 55 times more stable than the conventional reference catalyst #2. The deactivation rate is calculated based on the data from stability tests. For example, for the reference catalyst #2, the reaction rate constant at the beginning and the end of the run, k1 and k2 were determined using the equation: k=−Ln(1−X$_{O2}$/100), where X$_{O2}$ is the oxygen conversion, and the deactivation rate of this catalyst is determined by using the equation: deactivation rate=[(k1−k2)/k1]/(t2−t1), where t2−t1 is the time duration between these two results, and where the deactivation rate was found to be 0.066 hr$^{-1}$. Similarly, the deactivation rate was determined for the multilayer catalyst #3 (i.e., a deactivation rate of 0.0012 hr$^{-1}$). The ratio of 55 is the ratio of the deactivation rates of conventional reference catalyst #2 and catalyst #3.

Figure 5:
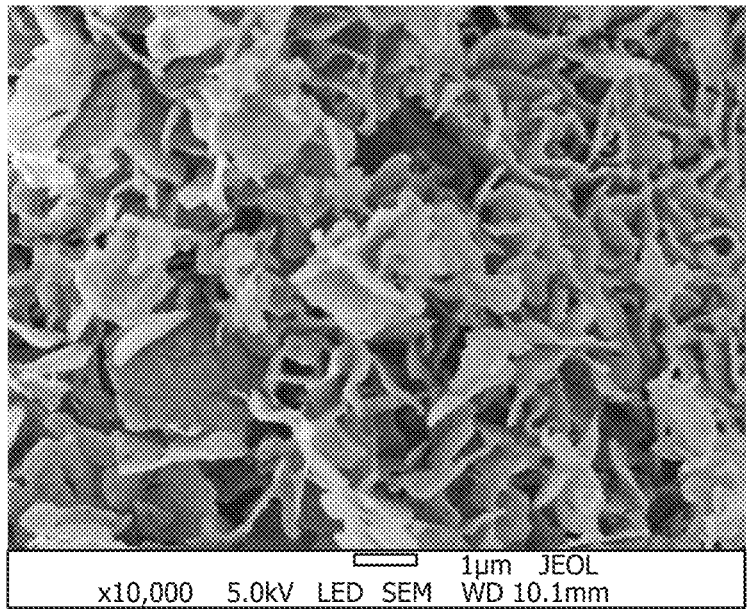
FIG. 5 displays a scanning electron microscope (SEM) micrograph of a multilayer supported OCM catalyst composition.

Overall, compared against the conventional reference catalyst #2, the multilayer catalyst #3 demonstrated at least the following performance advantages: much higher activity as indicated by the ability to use a much higher WHSV as shown in Table 4; higher useful C$_{2+}$ selectivity; and much lower deactivation rate under much higher WHSV. Additionally, as described previously herein, the performance of the conventional reference catalyst #2 will drop significantly when it is scaled-up owing to an increase in density with compression, while the multilayer supported OCM catalyst compositions do not have this drawback. The high performance obtained with the multilayer supported OCM catalyst compositions as disclosed herein is related to its composition, for example its structure (e.g., multilayer structure, crystal structure, etc.). A scanning electron microscope (SEM) micrograph image of catalyst #5 is shown in FIG. 5. It can be seen that the multilayer catalyst #5 displays sheet-like crystals on the surface of the catalyst. Such sheet-like structure has very high external surface area, which makes the active sites to be easier accessible by the reactants, resulting in higher activity. At the same time, such crystal structure allows methyl radicals to leave the active sites easier, resulting in better selectivity.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A multilayer supported oxidative coupling of methane (OCM) catalyst composition characterized by the general formula A$_a$Z$_b$E$_c$D$_d$O$_x$/support, wherein the multilayer supported OCM catalyst composition comprises a support, a first single oxide layer, one or more mixed oxide layers, and an optional second single oxide layer;

wherein A is an alkaline earth metal; wherein Z is a first rare earth element; wherein E is a second rare earth element; wherein D is a redox agent or a third rare earth element; wherein the first rare earth element, the second rare earth element, and the third rare earth element, when present, are not the same; wherein a is 1.0; wherein b is from about 0.1 to about 10.0; wherein c is from about 0.1 to about 10.0; wherein d is from about 0 to about 10.0; wherein x balances the oxidation states;

wherein the first single oxide layer contacts the support and the one or more mixed oxide layers, wherein the first single oxide layer is characterized by the general formula $Z_{b1}O_{x1}$, wherein b1 is from about 0.1 to about 10.0; and wherein x1 balances the oxidation states;

wherein the one or more mixed oxide layers contacts the first single oxide layer and optionally the second single oxide layer, wherein the one or more mixed oxide layers is characterized by the general formula $A_{a2}Z_{b2}E_{c2}D_{d2}O_{x2}$, wherein a2 is 1.0; wherein b2 is from about 0.1 to about 10.0; wherein c2 is from about 0.1 to about 10.0; wherein d2 is from about 0 to about 10.0; wherein x2 balances the oxidation states; wherein the general formula $A_aZ_bE_cD_dO_x$ and the general formula $A_{a2}Z_{b2}E_{c2}D_{d2}O_{x2}$ are different;

wherein the second single oxide layer, when present, contacts the one or more mixed oxide layers and optionally the first single oxide layer, and wherein the second single oxide layer is characterized by the general formula AO.

2. The multilayer supported OCM catalyst composition of claim 1, wherein the alkaline earth metal is selected from the group consisting of magnesium (Mg), calcium (Ca), strontium (Sr), barium (Ba), and combinations thereof.

3. The multilayer supported OCM catalyst composition of claim 1, wherein the first rare earth element, the second rare earth element, and the third rare earth element can each independently be selected from the group consisting of lanthanum (La), scandium (Sc), cerium (Ce), praseodymium (Pr), neodymium (Nd), promethium (Pm), samarium (Sm), europium (Eu), gadolinium (Gd), yttrium (Y), terbium (Tb), dysprosium (Dy), holmium (Ho), erbium (Er), thulium (Tm), ytterbium (Yb), lutetium (Lu), and combinations thereof.

4. The multilayer supported OCM catalyst composition of claim 1, wherein the redox agent is selected from the group consisting of manganese (Mn), tungsten (W), bismuth (Bi), antimony (Sb), tin (Sn), cerium (Ce), praseodymium (Pr), and combinations thereof.

5. The multilayer supported OCM catalyst composition of claim 1, wherein the first single oxide layer comprises $La_2O_3$.

6. The multilayer supported OCM catalyst composition of claim 1, wherein the second single oxide layer comprises SrO.

7. The multilayer supported OCM catalyst composition of claim 1, wherein the one or more mixed oxide layers has the general formula $Sr_{a2}La_{b2}Yb_{c2}Nd_{d2}O_{x2}$; wherein a2 is 1.0; wherein b2 is from about 0.1 to about 10.0; wherein c2 is from about 0.1 to about 10.0; wherein d2 is from about 0 to about 10.0; and wherein x2 balances the oxidation states.

8. The multilayer supported OCM catalyst composition of claim 1, wherein the support is selected from the group consisting of alumina ($Al_2O_3$), silica ($SiO_2$), silica ($SiO_2$)-alumina ($Al_2O_3$), silicon carbide (SiC), zirconia ($ZrO_2$), titania ($TiO_2$), magnesium oxide (MgO), zeolites, transition metal oxides, alkali metal oxides, alkaline earth metal oxides, lanthanide oxides, actinide oxides, carbon, and combinations thereof.

9. The multilayer supported OCM catalyst composition of claim 1, wherein the support has a surface area in a range of from greater than 0 m²/g and less than about 20.0 m²/g, as determined by measuring nitrogen adsorption according to the Brunauer, Emmett and Teller (BET) method.

10. The multilayer supported OCM catalyst composition of claim 1, wherein the support has a total pore volume in a range of from about 0.1 cc/g to about 1.0 cc/g, as determined by measuring nitrogen adsorption according to the BET method.

11. The multilayer supported OCM catalyst composition of claim 1, wherein the support has a pore size distribution in a range of from about 0.01 microns to about 500 microns, as determined by measuring nitrogen adsorption according to the BET method.

12. The multilayer supported OCM catalyst composition of claim 1, wherein the weight ratio of $A_aZ_bE_cD_dO_x$ to the support is in a range of from about 0.01 to about 5.0.

13. The multilayer supported OCM catalyst composition of claim 1, wherein (1) the first single oxide layer is characterized by a thickness of from about 0.001 μm to about 100 μm, (2) the one or more mixed oxide layers is characterized by a thickness of from about 0.002 μm to about 250 μm, (3) the second single oxide layer is characterized by a thickness of from about 0.001 μm to about 50 μm, or (4) any combinations of (1)-(3).

14. A method of making a multilayer supported oxidative coupling of methane (OCM) catalyst composition comprising:

(a) contacting a support with a first OCM catalyst precursor mixture to form a first supported OCM catalyst precursor, wherein the first OCM catalyst precursor mixture comprises one or more compounds comprising a first rare earth element cation (Z);

(b) calcining at least a portion of the first supported OCM catalyst precursor at a temperature of equal to or greater than about 500° C. to form a first calcined supported OCM catalyst precursor, wherein the first calcined supported OCM catalyst precursor comprises the support and a first single oxide layer, wherein the first single oxide layer contacts the support, wherein the first single oxide layer is characterized by the general formula $Z_{b1}O_{x1}$, and wherein b1 is from about 0.1 to about 10.0; and wherein x1 balances the oxidation states;

(c) contacting at least a portion of the first calcined supported OCM catalyst precursor with a second OCM catalyst precursor mixture to form a second supported OCM catalyst precursor, wherein the second OCM catalyst precursor mixture comprises one or more compounds comprising an alkaline earth metal cation, one or more compounds comprising the first rare earth element cation (Z), one or more compounds comprising a second rare earth element cation (E), and one or more compounds comprising a redox agent cation or a third rare earth element cation (D); wherein the first rare earth element cation, the second rare earth element cation, and the third rare earth element cation, when present, are not the same; wherein the second OCM catalyst precursor mixture is characterized by a molar ratio of first rare earth element to alkaline earth metal of b2:1, wherein b2 is from about 0.1 to about 10.0; wherein the second OCM catalyst precursor mixture is characterized by a molar ratio of second rare earth element to alkaline earth metal of c2:1, wherein c2 is from about 0.1 to about 10.0; and wherein the second OCM catalyst precursor mixture is characterized by a molar ratio of redox agent or third rare earth element to alkaline earth metal of d2:1, wherein d2 is from about 0 to about 10.0; and (d) calcining at least a portion of the second supported OCM catalyst precursor at a temperature of equal to or greater than about 500° C. to form the multilayer supported OCM catalyst composition of claim 1 or a second calcined supported OCM precursor.

15. The method of claim 14 further comprising (a1) solubilizing the one or more compounds comprising a first rare earth element cation in an aqueous medium to form the first OCM catalyst precursor mixture; and (a2) drying at least a portion of the first OCM catalyst precursor at a temperature of equal to or greater than about 75° C. prior to step (b) of calcining the first supported OCM catalyst precursor.

16. The method of claim 14 further comprising (c1) solubilizing the one or more compounds comprising an alkaline earth metal cation, one or more compounds comprising a first rare earth element cation, one or more compounds comprising a second rare earth element cation, and one or more compounds comprising a redox agent cation or a third rare earth element cation in an aqueous medium to form the second OCM catalyst precursor mixture; and (c2) drying at least a portion of the second supported OCM catalyst precursor at a temperature of equal to or greater than about 75° C. prior to step (d) of calcining the second supported OCM catalyst precursor.

17. The method of claim 14 further comprising repeating steps (c) and (d) as necessary to achieve a target thickness for the one or more mixed oxide layers.

18. The method of claim 14, wherein calcining at least a portion of the second supported OCM catalyst precursor at a temperature of equal to or greater than about 500° C. yields the second calcined supported OCM catalyst precursor; and further comprising:
  (d) contacting at least a portion of the second calcined supported OCM catalyst precursor with a third OCM catalyst precursor mixture to form a third supported OCM catalyst precursor, wherein the third OCM catalyst precursor mixture comprises one or more compounds comprising an alkaline earth metal cation; and
  (e) calcining at least a portion of the third supported OCM catalyst precursor at a temperature of equal to or greater than about 500° C. to form the multilayer supported OCM catalyst composition.

19. A method for producing olefins comprising:
(a) introducing a reactant mixture to an oxidative coupling of methane (OCM) reactor comprising the multilayer supported OCM catalyst composition of claim 1, wherein the reactant mixture comprises methane ($CH_4$) and oxygen ($O_2$);
(b) allowing at least a portion of the reactant mixture to contact at least a portion of the multilayer supported OCM catalyst composition and react via an OCM reaction to form a product mixture comprising unreacted methane and olefins;
(c) recovering at least a portion of the product mixture from the OCM reactor; and
(d) recovering at least a portion of the olefins from the product mixture.

20. A method for producing olefins comprising:
(a) introducing a reactant mixture to an oxidative coupling of methane (OCM) reactor comprising the multilayer supported OCM catalyst composition of claim 7, wherein the reactant mixture comprises methane ($CH_4$) and oxygen ($O_2$);
(b) allowing at least a portion of the reactant mixture to contact at least a portion of the multilayer supported OCM catalyst composition and react via an OCM reaction to form a product mixture comprising unreacted methane and olefins;
(c) recovering at least a portion of the product mixture from the OCM reactor; and
(d) recovering at least a portion of the olefins from the product mixture.

* * * * *